United States Patent
Saitoh et al.

(10) Patent No.: US 9,585,805 B2
(45) Date of Patent: Mar. 7, 2017

(54) PROCESSING EQUIPMENT OF EXCRETORY SUBSTANCES AND THE METHOD

(75) Inventors: Tokuo Saitoh, Miyagi (JP); Fumiyuki Akoshima, Migagi (JP); Kiichi Komatsu, Akita (JP); Nobuyoshi Kurosawa, Tokyo (JP)

(73) Assignee: Keiko Saitoh, Miyagi (JP)

( * ) Notice: Subject to any disclaimer, the term of this patent is extended or adjusted under 35 U.S.C. 154(b) by 0 days.

(21) Appl. No.: 14/389,558

(22) PCT Filed: Apr. 2, 2012

(86) PCT No.: PCT/JP2012/058950
§ 371 (c)(1),
(2), (4) Date: Nov. 26, 2014

(87) PCT Pub. No.: WO2013/150588
PCT Pub. Date: Oct. 10, 2013

(65) Prior Publication Data
US 2015/0328072 A1 Nov. 19, 2015

(51) Int. Cl.
*A61G 9/00* (2006.01)
*A61F 5/441* (2006.01)
*A61F 5/451* (2006.01)

(52) U.S. Cl.
CPC .............. *A61G 9/00* (2013.01); *A61F 5/441* (2013.01); *A61F 5/451* (2013.01); *A61G 2203/30* (2013.01); *A61G 2203/46* (2013.01)

(58) Field of Classification Search
CPC .... A61F 5/4401; A61F 5/4404; A61F 5/4405; A61F 5/4408; A61F 5/441; A61G 9/00
(Continued)

(56) References Cited

U.S. PATENT DOCUMENTS

| 6,110,159 A | 8/2000 | Tsujita et al. |
| 6,554,817 B1 * | 4/2003 | Oki .................. A61G 9/00 4/455 |

(Continued)

FOREIGN PATENT DOCUMENTS

| EP | 0 894 483 | 2/1931 |
| JP | 2002-113030 | 4/2002 |

(Continued)

*Primary Examiner* — Janie Loeppke
(74) *Attorney, Agent, or Firm* — Jordan and Koda, PLLC

(57) ABSTRACT

To provide a compact type of equipment with less noise by which stool of a person receiving care can be processed surely without the person's unpleasant sensation regardless of stool's nature, reducing the load on the person receiving care. In the processing equipment of excretory substances, the suction circulation tube is led to the cooling unit outside the device house box from the discharge side of the suction motor and cooled down by heat exchange with outer air inside the cooling unit, and then returned to the return box unit. The defecation sensor comprises a sensor which detects stool's hardness to control in order to vacuum up at the setting with the higher suction power for signals of harder stool. The urination sensor comprises a sensor which has two contact points to calculate a necessary suction power according to the degree of the signals and control. Moreover, the suction motor, cooling fan, and filter inside the suction motor unit are covered by highly rigid vibration-suppression material processed by vibration preventive material, placed on vibration preventive board, and held with suspension by the vibration preventive spring.

20 Claims, 15 Drawing Sheets

(58) Field of Classification Search
USPC .................................................. 4/319–322
See application file for complete search history.

(56) References Cited

U.S. PATENT DOCUMENTS

| | | | |
|---|---|---|---|
| 8,904,571 B2* | 12/2014 | Moore | E03D 5/016 4/317 |
| 2002/0010446 A1* | 1/2002 | Maimets | A61F 5/451 604/355 |
| 2004/0199131 A1 | 10/2004 | Kitamura | |
| 2008/0178377 A1* | 7/2008 | Liu | A47K 11/02 4/450 |
| 2010/0174250 A1* | 7/2010 | Hu | A61F 5/4401 604/319 |

FOREIGN PATENT DOCUMENTS

| | | |
|---|---|---|
| JP | 2003-153931 | 5/2003 |
| JP | 2006-141590 | 6/2006 |
| JP | 2007-312920 | 12/2007 |
| JP | 3144371 | 8/2008 |
| JP | 2009-188505 | 8/2009 |
| JP | 2010-284498 | 12/2010 |
| WO | WO-2006/046532 | 5/2006 |

\* cited by examiner (a) Wave shape of urine detection (b) Wave shape of soft stool detection (c) Wave shape of hard stool detection (d) Wave shape of suction of ordinary sewage water (e) Wave shape of suction of large amount of hard stood

PROCESSING EQUIPMENT OF EXCRETORY SUBSTANCES AND THE METHOD

BACKGROUND OF THE INVENTION

The present invention relates to a processing equipment of excretory substances in people who require nursing care and the method. More particularly, the invention relates to a processing equipment of excretory substances in solitary old people at side lying position who cannot urinate/evacuate their bowels by themselves or people who cannot move and require severe nursing care, which processes their urines/feces automatically to keep them clean and reduce their unpleasant sensation; and which reduces labors by care personnel such as staffs of emergency facilities, nurses, family etc., reducing the necessity for them to always attend.

According to a survey in 2011, it is estimated that there are 4.6 million solitary old people. Not all the solitary old people require automatic processing equipment of excretory substances. In patients who are kept in care facilities and old people confined in bed who require nursing care, a processing equipment of excretory substances became required, in which their urination and defecation can be detected automatically and processed to always keep their groins clean.

In current situation, urines of patients confined to beds in care facilities and hospitals are treated in incontinent conditions in which a tube is inserted to the urinary tract and feces are defecated to napkins, which care personnel exchange to keep them clean. Although there have been only little problems in hospitals and care facilities having experienced care personnel, there are not a few patients who feel discomfort for urination and defecation assisted by other persons.

Recently, in Japan and Europe and U.S.A., where falling birthrate and aging have been advancing, physical and mental fatigues in care personnel induced by insufficient care personnel, increased load on cohabiters, care of old person by old person etc. have become problem and distressing cases have been increasing. In such situation, development of processing equipment of excretory substances has become an urgent need.

Conventionally, many patent applications in this field relating to persons confined to beds who require care have existed. However, in current situation, those products cannot be better than ordinary napkins in points of wearing condition, maintaining cleanness, bed sore, operation failure of equipment, maintenance condition etc., so that those have not come into practical use.

In conventional processing equipment of excretory substances, there are some equipment described in patent documents 1, 2, and 3. The invention written in the patent document 1 is an automatic processing equipment of excretory substances for old people confined to bed, which comprises a sewage storage tank, suction equipment, cleaning equipment, napkin cup etc. However, as for equipment related to the invention, major problems associated with this type of processing equipment of excretory substances such as noise, vibration, bacteria elimination, excessive heating of motor, patient's comfort, maintenance of equipment etc. are hardly described.

The invention described in the patent document 2 is a method to apply an adhesive around mounting holes in order to paste the mounting hole's surrounding of napkin with the cup. Adhesive can be applied directly to napkin or a tape in which adhesive is applied to both the sides can be applied to napkin. The face of adhesive is protected by pasted release paper and, the release paper is removed for use and the application face of adhesive is pasted to the cup. As such, because the application face of adhesive is pasted to the cup, it is stated that there are effects that the cup and napkin can be connected very simply and it is unlikely to leak liquid.

In the patent document 3, it was written that there were proposals including improvement of cleaning ability by hot water, prevention of inflow of motor-brush's abrasion powder into the cup main body by means of separate blasts of work wind (flow of air with suction and circulation) and cooling wind, prevention of outflow of sewage tank to outside etc, and its trial sales were conducted.

The automatic processing equipment of urination and defecation will be explained, based on FIGS. 14, 15, and 16.

FIG. 16 shows an outline illustrative diagram of the whole equipment. FIGS. 14 and 15 show perspective views and cross-section views of a napkin cup main body 10 and a napkin 54, respectively.

When excretory substances are detected by defecation sensor 13 and urination sensor 14 existing at a concave part receiving excretory substances 77 in the napkin cup main body 10, a water pump 39 of a water supply unit 25 operates to supply hot water for cleaning through a rinse solution hose 20 to the inside of the napkin cup main body 10 and at the same time, a suction motor 31 of a suction motor unit 24 operates to vacuum up air from the inside of a sewage-water tank 22 through a sewage suction hose 15 and a suction circulation tube 50. As the result, a suction power occurs inside the sewage suction hose 15 and the suction circulation tube 50 to vacuum up excretory substances of the concave part receiving excretory substances 77 in the napkin cup main body 10 and sewage water after cleaning. Said excretory substances and sewage water after cleaning are then vacuumed up into the inside of the sewage-water tank 22 and stored. Inside the sewage tank 22, said excretory substances and sewage water after cleaning are separated with gravitation by the work wind circulating through the suction circulation tube 50.

When said suction motor 31 operates, circulating air flow occurs in such a manner that air from the concave part receiving excretory substances 77 in the napkin cup main body 10 reaches the suction motor 31 through the sewage suction hose 15, the sewage water tank unit 22 and a cleanup processing unit 23 and moreover returns to the inside of said napkin cup main body 10 through the suction circulation tube 50 and a return air hose 18.

When said suction motor 31 operates, the work wind of the suction circulation tube 50 which was introduced from a suction hole of said suction motor 31 passes through the suction motor 31 to receive endotherm; then passes through a discharge hole of the suction motor 31, a return air cooler 26, and a return box unit 27; and flows out to the inside of the napkin cup main body 10 through a return air hose 18.

As for the work wind vacuumed up from said suction motor 31, about 10% is discharged from the return box unit 27 through a discharge hose 19. The remaining 90% passes through the return box unit 27 and the return air hose 18 and returns to the napkin cup main body 10 from a blast hole. That is, air is vacuumed up from a gap between a napkin 54 in the napkin cup main body 10 attaching to the person receiving care and the hip and approximates the same volume of air as vacuumed up air (about 10% of work wind) is released outside from the return box 27 and a discharge hose 19 partially.

As such, hot wind is sent to the inside of the napkin cup main body 10 through said return air hose 18.

To prevent for the suction motor 31 to be heated, cooling air is vacuumed up at a cooling fan 32 of the suction motor unit 24 from an intake hole of cooling wind 34 through a filter 33, cools down the suction motor 31, and is then discharged from a discharge hole of cooling air 35.

Therefore, comfortable cleaning can be done in a condition that hot wind exists around the waist and hip of the person receiving care.

PRIOR ART DOCUMENTS

Publication of JP unexamined patent application No. 2002-113030
Publication of JP unexamined patent application No. 2006-441590
Publication of JP unexamined patent application No. 3144371

SUMMARY OF THE INVENTION

Because the equipment written in the literature 3 is designed to house the whole equipment compactly as a major purpose, there is some problem in its maintenance. As other problems, because it has a closed structure to prevent motor's noise and vibration, the cooling effect of the cooler which cools down work wind directly is so insufficient that excessive heating of the suction motor might bring down the equipment. Once excessive heating occurs, the temperature of the suction motor needs to be decreased to about 50° C. for re-operation, which takes about 30 minutes. It is a problem in its practicability.

And there are two types in processing equipment of excretory substances in people who require nursing care. A type is to sit down on toilet stool assisting by care personal can evacuate and washes automatically afterward. The other type is that are defecated to napkin wrapped hips of people who require nursing care and washes and dries automatically.

In the well-known second type, there are not satisfactory equipment all of prevention of bed sore difference of napkins form concern with difference of figure (man, woman, Japanese, Westerner, etc.), stool's hardness, feeling of wearing condition, simplicity of put on and take off of napkin, safety and endurance of equipment, noise, maintenance cleanness, bad smell, peace of mind, etc.

The purposes of this present invention are to reduce discomfort of persons requiring nursing cares, prevent their bed sore, reduce the burden of care personnel by means of automatic processing of excretory substances for immovable persons requiring nursing care such as postoperative patients, solitary old persons, or persons with partial paralysis who cannot do urination and defecation by themselves; and moreover, to provide a compact-type equipment having easy maintenance of constructive devices with less noise and which is usable at hospitals where multiple inpatients receive cares within a room.

A processing equipment of excretory substances, comprising a sewage water tank unit 22, a cleanup processing unit 23, a suction motor unit 24, a water supply unit 25, and a return box unit 27 in a device house box 12 connected to a napkin cup main body 10 by a hose unit 11; in which rinse solution sent from a water supply pump 39 in said water supply unit 25 is sprayed to the inside of a napkin cup main body 10, the urinary organ and excretory substances are washed in the napkin cup main body, sewage is vacuumed up by work wind of a suction motor 31 closed and isolated inside said suction motor unit 24, sewage is divided into excretory substances and rinse solution and housed them separately in said sewage water tank unit 22, and only said work wind is cleaned up in the cleanup processing unit 23 and returned to said napkin cup main body 10 through the suction motor 31 and return box unit 27 by suction circulation tube 50; wherein said suction circulation tube 50 is led to a cooling unit 55 mounted outside said device house box 12 from the discharge side of said suction motor 31, is cooled down by heat exchange with outer air inside the cooling unit 55, and then returned to said return box unit 27.

The processing equipment of excretory substances according to claim 1, equipping the cooling unit 55 comprising a box-like cooling box 61 like a metal box with a good heat conduction in which the suction circulation tube 50 curved is arranged.

A slight wind circulation tube 51 is mounted along the suction circulation tube 50 circulating from the napkin cup main body 10 to the napkin cup main body 10 through the sewage water tank unit 22, cleanup processing unit 23, cooling unit 55, and return box unit 27; and a slight wind motor 48 by which slight wind for drying circulates when the suction motor 31 doesn't operate is mounted at the slight wind circulation tube 51 inside said return box unit 27.

Said cleanup processing unit 23, the suction motor unit 24, the water supply unit 25, and the return box unit 27 are made independent units and housed inside the device house box 12 and also connected in order in a detachable manner; said sewage water tank unit 22 is separated from said device house box 12, made a unit, and connected to said cleanup processing unit 23 in a detachable manner.

A flat box-like cooling box 61 doubled with a seat on which the device house box 12 and the sewage water tank unit 22 are placed and of which the caster 70 is mounted at the bottom face.

Moreover a concave part receiving excretory substances is mounted in the napkin cup main body 10, a defecation sensor 13 and an urination sensor 14 are equipped at the concave part, said defecation sensor 13 is mounted at a site of stool's falling, comprising a sensor to detect stool's hardness in order to control the suction of excretory substances at a setting of suction power with a higher suction power for higher signals of stool's hardness by the control panel unit 56, said urination sensor 14 comprising a sensor evaluates for presence or absence of urine and has two contact points to control at the control panel unit 56 in order to calculate a necessary suction power for vacuuming up excretory substances according to the degree of the signals and measures the resistance between the two points.

And moreover, the processing operation can be conducted by any of the modes including a frequent urination mode that the suction motor 31 drives when the sensed signals are shorter than a set time of said urination sensor 14 without sensed signals of said defection sensor 13, minor mode that the suction motor 31 drives when sensed signals are higher than a set time of said urination sensor 14, and major mode that the suction motor 31 drives when sensed signals of said defection sensor 13 is present.

In the frequent urination mode, the suction motor 31 drives when sensed short signals at each set time of the urination sensor 14 are less than set number of times. In the minor mode, when sensed short signals at each set time of urination sensor 14 are higher than set number of times, the suction motor 31 drives intermittently to clean multiple times.

In the major mode, when sensed signals of the defecation sensor 13 are present and the suction motor 31 drives intermittently to clean multiple time, if the rinse solution is insufficient, set number of times is reduced to clean.

The suction motor operates intermittently with a unit of several minutes each for driving and stop.

A processing equipment of excretory substances, comprising a sewage water tank unit 22, a cleanup processing unit 23, a suction motor unit 24, a water supply unit 25, and a return box unit 27 in a device house box 12 connected to a napkin cup main body 10 by a hose unit 11; in which rinse solution sent from a water supply pump 39 in said water supply unit 25 is sprayed to the inside of a napkin cup main body 10, the urinary organ and excretory substances are washed in the napkin cup main body, sewage is vacuumed up by work wind of a suction motor 31 closed and isolated inside said suction motor unit 24, sewage is divided into excretory substances and rinse solution and housed them separately in said sewage water tank unit 22, and only said work wind is cleaned up in the cleanup processing unit 23 and returned to said napkin cup main body 10 through the suction motor 31 and return box unit 27 by suction circulation tube 50, wherein said suction circulation tube 50 is led to a cooling unit 55 mounted outside said device house box 12 from the discharge side of said suction motor 31, is cooled down by heat exchange with outer air inside the cooling unit 55, and then returned to said return box unit 27; Conventional equipment has a closed configuration to prevent noise and vibration and odor to be released outside, which causes a major problem to halt the circulation air due to excessive heating of the motor 31. The present invention enables to prevent the defect by non-motive engine cooler in which the suction circulation tube 50 passes through the cooling unit 55.

According to the invention, the cooling unit 55 comprises the cooling box 61 like a box made from a metal with good thermal conductor or others and the suction circulation tube 50 is arranged in a bending curvature condition inside the cooling box 61. Thus, the whole equipment doesn't take up much space and a high cooling effect can be obtained.

According to the invention, a slight wind circulation tube is arranged along, the suction circulation tube which circulates from the napkin cup main body 10 to the napkin cup main body through the sewage water tank unit, cleanup processing unit, cooling unit and return box unit; and a slight wind motor which circulates slight wind for drying at non-operation of the suction motor is arranged at the slight wind circulation tube inside said return box unit. Thus, rinse solution for washing the hip of person receiving care and sent wind air for drying the hip and the napkin cup main body are controlled for temperature, so that the person receiving care doesn't feel discomfort.

According to the invention, because multiple fans which conducts heat exchange with outer air are installed at the suction circulation tube 50 and the slight wind circulation 51 inside the cooling box 61, the heat exchange can be done efficiently by simple configuration.

According to the invention, a partial discharge hose 19 through which partial work wind circulates is connected to the suction circulation tube 50 and the same volume of air as the discharged wind is vacuumed up at the napkin cup main body 10 from outside. Thus, as the temperature of circulating air is kept appropriately, new air can be always supplied.

According to the invention, said cleanup processing unit 23, the suction motor unit 24, the water supply unit 25 and the return box unit 27 are made independent units and housed inside the device house box 12 and also connected in order in a detachable manner; said sewage water tank unit 22 is separated from. said device house box 12, made a unit, and connected to said cleanup processing unit 23 in a detachable manner.

In the equipment written in cited reference 3, once excessive heating occurs, the temperature of the suction motor needs to he decreased to about 50° C. for re-operation, which takes about 30 minutes. It is a problem in its practicability In this invention, as such, pipes and wirings connecting the units are set in unification and one-touch detachable manners, which facilitates nit exchange such as due to failure, reintegration from the maintenance, treatment of excretory substances from the sewage water tank unit 22 for taking those to disposal station etc. In addition, the napkin cup main body 10 and the devices are separated and connected by the hose unit 11, so that the driving part of the processing equipment of excretory substances can be placed at a position where care personnel and care workers are not disturbed and there is no trouble for persons receiving care to get into touch with the equipment.

According to the invention, the cooling box 61 which is flat-box like doubles with a pedestal on which the device-house box 12 and the sewage water tank unit 22 are placed and a caster 70 is installed on the bottom face of the cooling box 61, so that the whole equipment becomes compact, which facilitates its indoor moving.

According to the invention, a concave part receiving excretory substances is mounted in the napkin cup main body 10, a defecation sensor 13 and an urination sensor 14 are equipped at the concave part, said defecation sensor 13 is mounted at a site of stool's falling, comprising a sensor to detect stool's hardness in order to control the suction of excretory substances at a setting of suction power with a higher suction power fir higher signals of stool's hardness by the control panel unit 56, said urination sensor 14 comprising a sensor evaluates for presence or absence of urine and has two contact points to control at the control panel unit 56 in order to calculate a necessary suction power for vacuuming up excretory substances according to the degree of the signals and measures the resistance between the two points.

What is important at vacuuming up sewage is that suction power, makeup water, and sprayed air volume are subtly different according to nature of the sewage. Especially, the degree of stool's hardness influences the suction power greatly. In the present invention, the configuration described above is designed to control the suction motor according to stool's weight and degree of impact shock and to avoid pains in the person receiving care which are caused by insufficient or excessive suction. That is, when the stool/urine detection equipment installed at the napkin cup in the equipment of the present invention detects stool or urine, conditions of the excretory substances (urine, soft stool, hard stool, or mixed stool and urine) are evaluated and the sewage suction power can be set automatically to prevent burden on the patient.

Moreover, the defecation sensor comprises one or more of a photo-reflector, a strain sensor, acceleration sensor or others. The urination sensor comprises the contact point sensor to measure the resistance between the two contact points and the suction intensity of urination and defecation and the suction method can be decided from the values of the sensor.

According to the invention, a bimetal 57 is installed inside the return box unit 27, and when circulating air temperature exceeds an appropriate temperature for human body set in advance, the slight wind motor 48 rotates inversely to vacuum up heated air of the napkin cup main body 10 from the slight wind hose 17 and discharges the air through the slight-wind discharge hose 21 to outdoor air. Thus, air blowing into the napkin cup main body can be always kept at an appropriate temperature for persons receiving care being always kept comfortably.

According to the invention, the napkin main body 10 is made from resin and the surface of the concave part receiving excretory substances are protected by a coating material which is stain-resistant, so that the concave part in the napkin cup main body can be always kept clean and troublesome works such as cleaning can be reduced.

According to the invention, because a partition plate to separate with gravity solid substances water from air with high humidity is installed inside the sewage water tank and a water-level sensor to notify the full level of excretory substances is also installed, the equipment can separate with gravity solid substances/water from air with high humidity and when the sewage water tank becomes full, the tank can be put on and off from the napkin cup main body and filter unit without any gap by one touch.

According to the invention, because a negative pressure sensor 52 Which detects if air leakage efficiency of the hoses connected to the napkin cup main body 10 is maintained, or if abnormality of each tank is present or absent, or if air leakage efficiency of the pipes is maintained to notify to care personnel or nurses by alarm on the display board.

According to the invention, the water supply unit 25 comprises the rinse solution tank 36, an supplementary tank 37, an water supply pump 39, a hot water tank 38, a valve 46, and a safe tank 40; in which a water level sensor 41 is installed at said supplementary tank 37 and a water level sensor 42 and a temperature sensor 43 and a heater 44 to make hot water are installed at said hot water tank 38, and a temperature sensor 45 is installed at said safe tank 40. Thus, the management of rinse solution such as temperature of the water and water volume of the tank etc. can be always kept normally.

According to the invention, because the equipment which collects biological information of a person receiving care and sends the information is installed near the napkin cup main body, information about urination and defection and information about heart rate and respiratory rate etc. in the person receiving care is installed, abnormal information about urination and defection and heart rate and respiratory rate etc. in the person can be obtained, and the degree of urination and defection desires, progression and recovery degrees of pathologic conditions, and sudden pathologic conditions in the person can he understood without installing a complex biologic information system which is used for patients with generally severe. conditions. The heart rate and respiratory rate can be calculated from subtle change in the pressure of the air sensor and those values can be compared with values at normal conditions, which enables to understand the information about urination and defecation desire in advance.

According to the invention, described in the processing equipment, the suction motor 31 and the cooling fan 32 and filter 33 inside the suction motor unit 24 are covered by rigid and vibration-proofing material and installed on a vibration-preventive board made from a vibration-proofing material and held with suspension by vibration-preventive spring 79, which enables to reduce high noise and vibration produced by the motor and pump used.

According to the invention, the equipment is designed for processing operation to select one of three modes; frequent urination mode driving the suction motor when sensed signal of the defecation sensor is absent and the sensed signal is shorter than the time set for the urination sensor, minor mode driving the suction motor when sensed signal of the defecation sensor is absent and the sensed signal is higher than the time set for urination sensor, and major mode driving the suction motor when sensed signal of the defecation sensor is present, As the result, the processing can he conducted appropriately according to kind of excretory substance, amount and size and energy saving can be also done.

According to the invention, the frequent urination mode is designed to drive the suction motor when short sensed signals at every time set for the urination sensor are less than the number set, so that the rinse solution isn't consumed away.

According to the invention, because the minor mode is designed to drive the suction motor intermittently and clean multiple times when short sensed signals at every time set for the urination sensor are the number set or more, the cleaning becomes surer.

According to the invention, in case that the major mode drives the suction motor intermittently and cleans the number of times set when sensed signals of the defecation are present, when rinse solution is insufficient, the cleaning is done reduced number of times set. Thus, the cleaning can be done even if the rinse solution becomes insufficient.

According to the invention, because the suction motor is designed to intermittently operate with driving and stopping at a unit of several minutes, the temperature of the suction motor doesn't increase unnecessarily to protect from accidents such as burn and for energy saving.

DETAILED DESCRIPTION OF THE PREFERRED EMBODIMENTS

Figure 1:
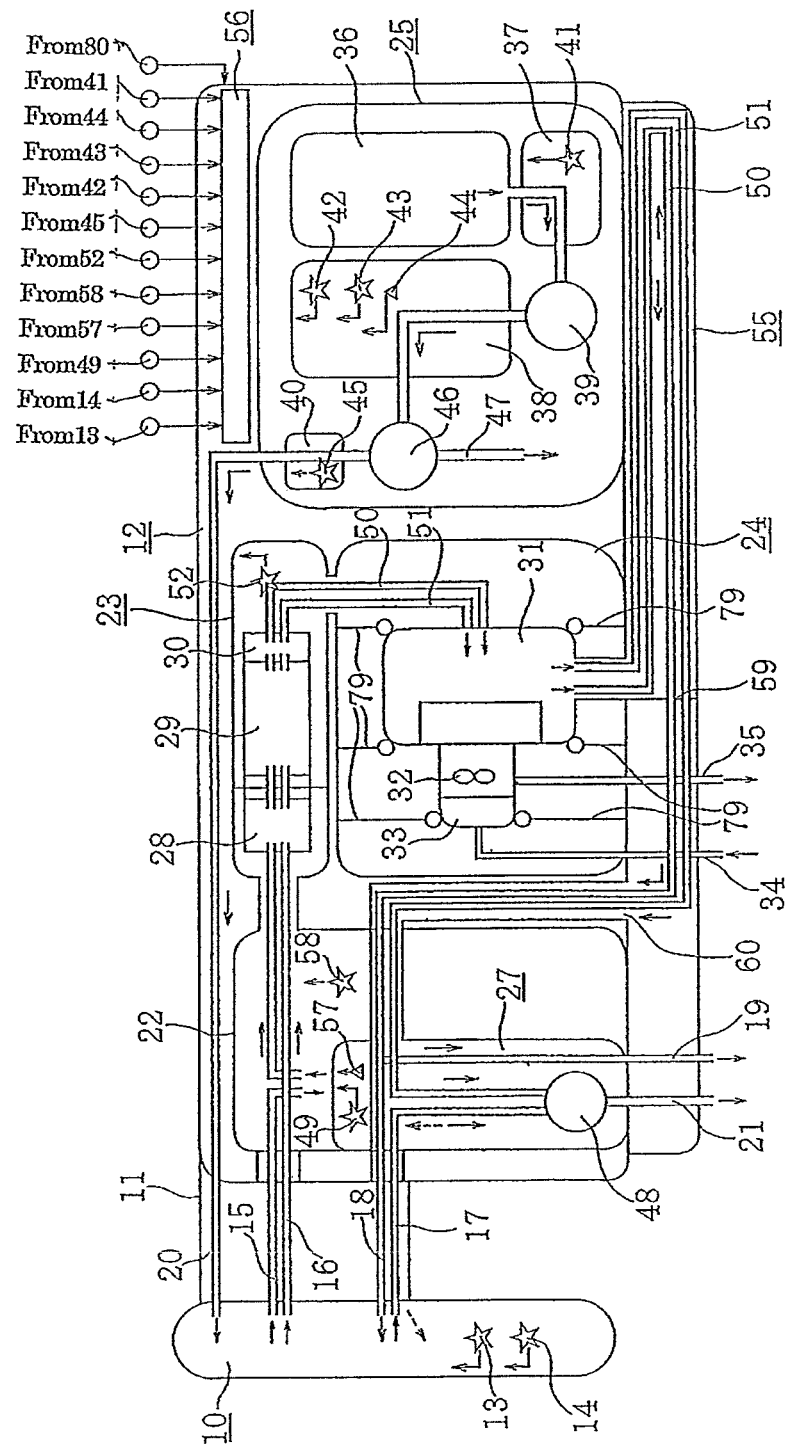
FIG. 1 shows a diagram of the lateral side in the example 1 of the processing equipment of excretory substances and methods relating to the present invention.

The present invention of the processing equipment of excretory substances has the device-house box 12 comprising the sewage water tank unit 22, cleanup processing unit 23, suction motor unit 24, water supply unit 25, and return box unit 27; in which the napkin cup main body 10 and device-house box 12 are connected by the hose unit 11, rinse solution sent from the water supply pump 39 in said water supply unit 25 is sprayed to the inside of the napkin cup main body 10 to clean the urinary organ and excretory substances in the napkin cup main body 10, the sewage is vacuumed up by work wind of the suction motor 31 closed and isolated inside said suction motor unit 24 and then divided into excretory substances and rinse solution inside said sewage-water tank unit 22 to be housed separately, only said work wind is cleaned up inside the cleanup processing unit 23 and then returned to said napkin cup main body 10 through the suction motor 31 and return box unit 27 by the suction circulation tube 50.

In the processing equipment of excretory substances, it is configured in such a manner that: said suction circulation tube 50 is led to the cooling unit 55 installed outside the said device-house box 12 from the discharge side of said suction motor 31, then cooled down by heat-exchange with outer air inside the cooling unit 55, and returned to said return box unit 27.

The cooling unit 55 comprises the cooling box 61 like a box made from a metal with good thermal conductor or others and the suction circulation tube 50 is arranged in a bending curvature condition inside the cooling box 61.

A slight wind circulation tube is arranged along the suction circulation tube which circulates from the napkin cup main body 10 to the napkin cup main body through the sewage water tank unit, cleanup processing unit, cooling unit and return box unit; and a slight wind motor which circulates slight wind for drying at non-operation of the suction motor is arranged at the slight wind circulation tube inside said return box unit.

Said cleanup processing unit 23, the suction motor unit 24, the water supply unit 25, and the return box unit 27 are made individually separate units and housed inside the device-house box 12, and are connected in order and in a detachable manner. Said sewage-water tank unit 22 is separated from said device-house box 12 to make it a unit and is connected to said cleaning processing unit 23 in a detachable manner.

The cooling box 61 which is flat-box like doubles with a pedestal on which the device-house box 12 and the sewage water tank unit 22 are placed and a caster 70 is installed on the bottom face of the cooling box 61.

The device house box equips the sewage water tank unit, cleanup processing unit, suction motor unit, water supply unit, and return box unit, and the napkin cup main body. In the processing equipment of excretory substances, the device house box are connected by the hose unit; rinse solution sent from the water supply pump in said water supply unit is sprayed to the inside of the napkin cup main body; the urinary organ and excretory substances are washed in the napkin cup main body and sewage are vacuumed up by work wind of the suction motor in said suction motor unit; excretory substances and rinse solution are separated from the sewage and housed in said sewage tank unit; and only said work wind is cleaned up at the cleanup processing unit and returned to said napkin cup main body through the suction motor and return box unit by the suction circulation tube. The concave part receiving excretory substances installed at the napkin cup main body equips the defecation sensor and urination sensor, in which said defecation sensor being at the bottom part of stool's falling detects stool's hardness for control in the control panel unit in order to vacuum up excretory substances with higher suction power for harder stool with higher signal, and said urination sensor having two contact points evaluates presence or absence of urine and calculates necessary suction power for vacuuming up excretory substances according to the degree of the signals to control in the control panel unit and measures the resistance between the points.

The equipment is designed for processing operation to select one of three modes; frequent urination mode driving the suction motor when sensed signal of the defecation sensor is absent and the sensed signal is shorter than the time set for the urination sensor, minor mode driving the suction motor when sensed signal of the defecation sensor is absent and the sensed signal is higher than the time set for urination sensor, and major mode driving the suction motor when sensed signal of the defecation sensor is present.

The frequent urination mode is designed to drive the suction motor when short sensed signals at every time set for the urination sensor are less than the number set.

The minor mode is designed to drive the suction motor intermittently and clean multiple times when short sensed signals at every time set for the urination sensor are the number set or more.

The major mode drives the suction motor intermittently and cleans the number of times set when sensed signals of the defecation are present, when rinse solution is insufficient, the cleaning is done reduced number of times set.

The suction motor is designed to intermittently operate with driving and stopping at a unit of several minutes.

EXAMPLE 1

Figure 2:
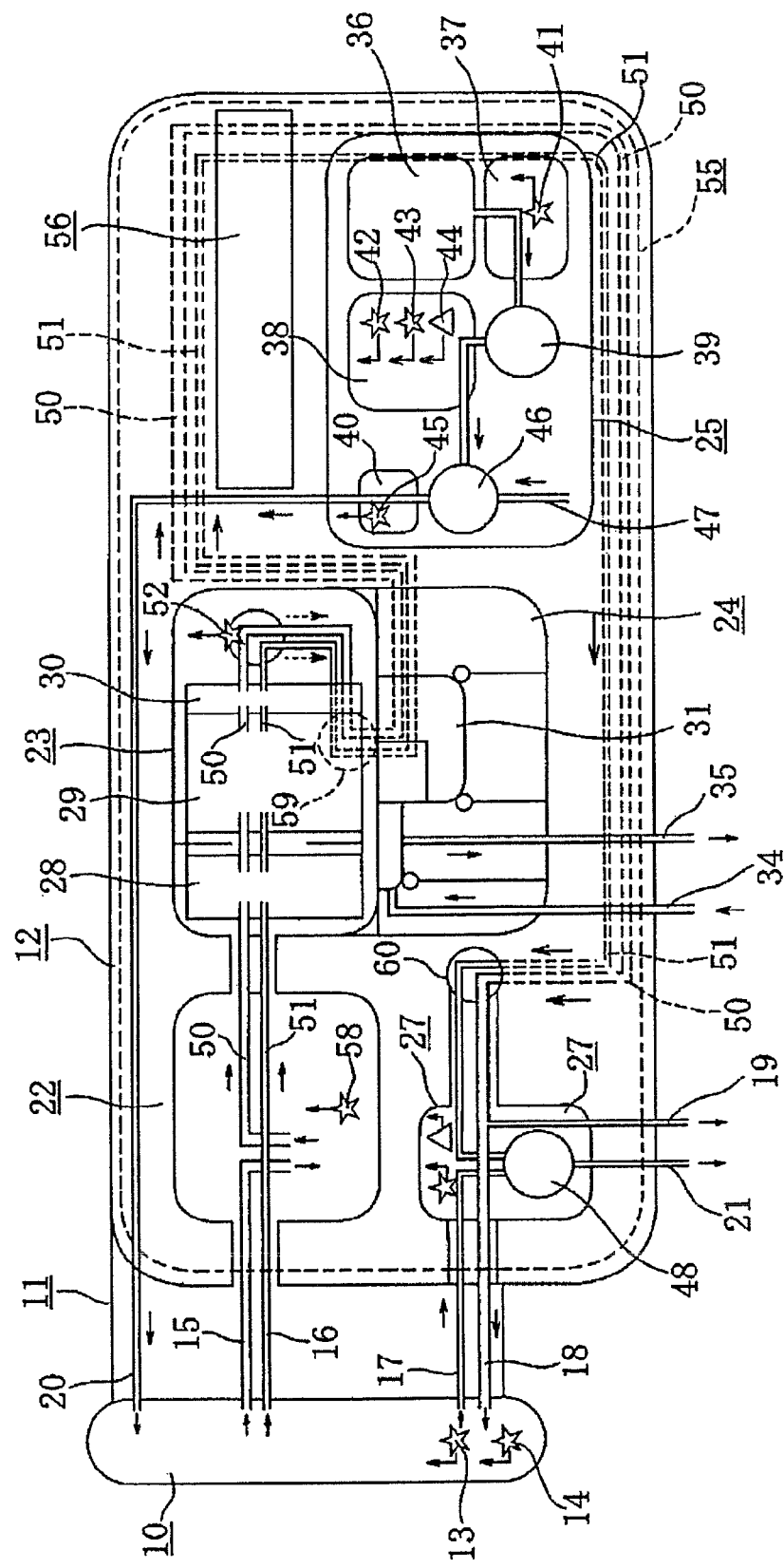
FIG. 2 shows a diagram of the plain surface in the example 1 of the processing equipment of excretory substances and methods relating to the present invention.
Figure 3:
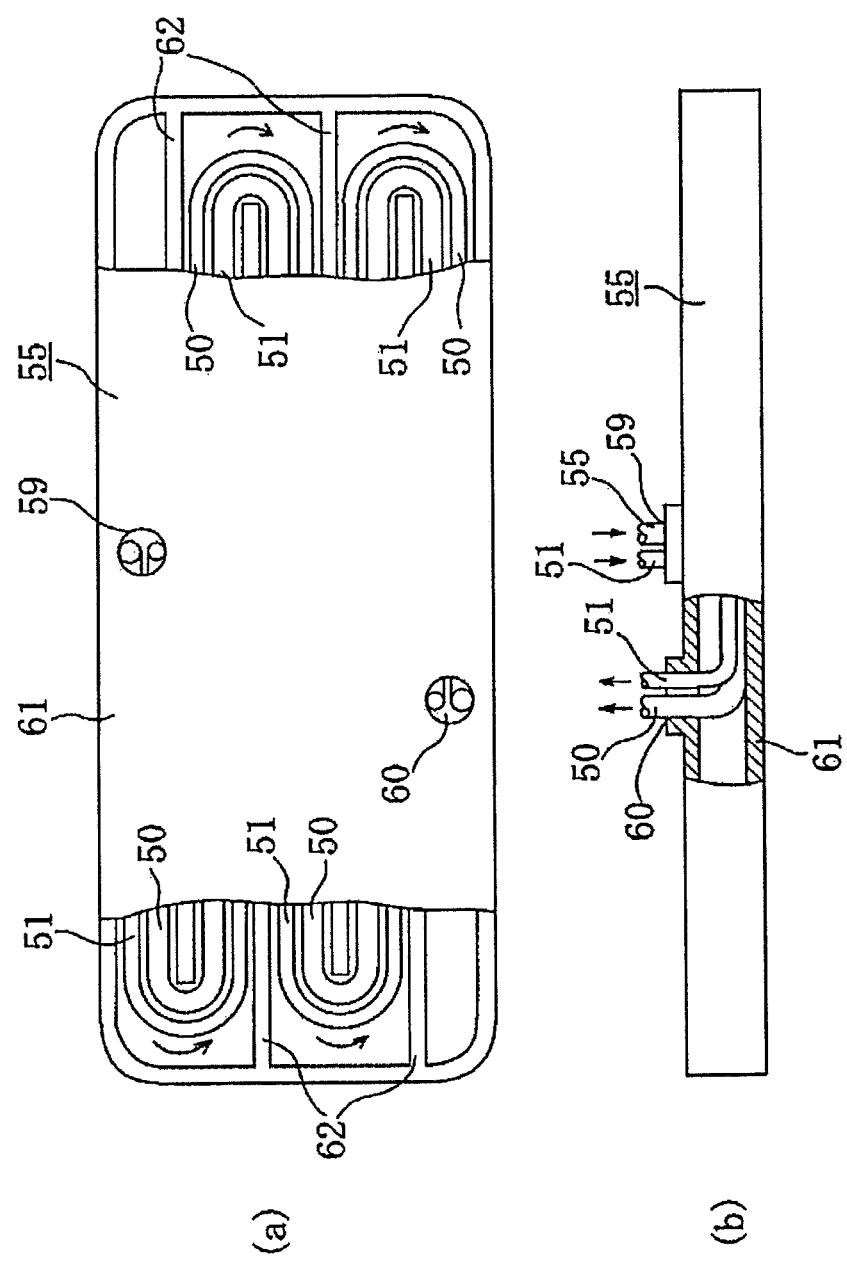
FIG. 3 shows a cooling unit equipped at the processing equipment of excretory substances and methods relating to the present invention, in which (a) shows a plain view lacking partially and (b) Shows a lateral view lacking partially.
Figure 4:
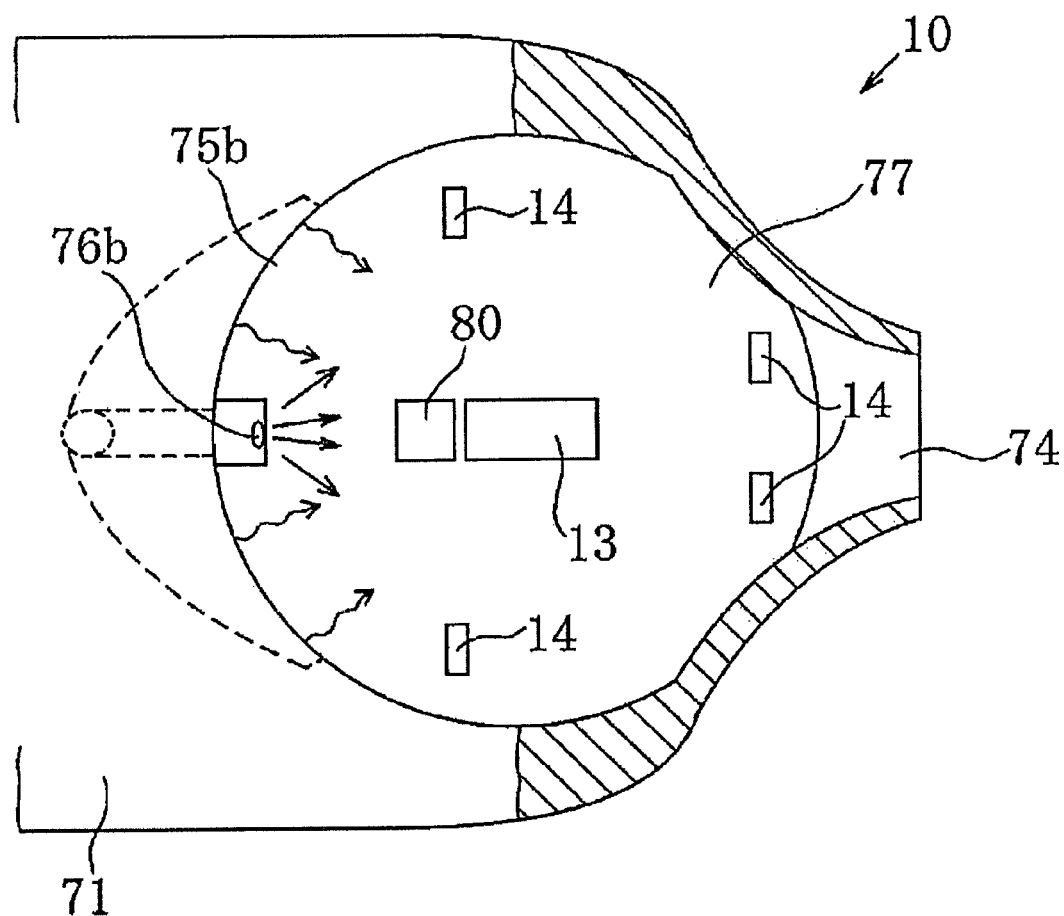
FIG. 4 shows a plain view lacking a part of the napkin cup main body 10 used for the processing equipment of excretory substances and methods relating to the present invention.
Figure 5:
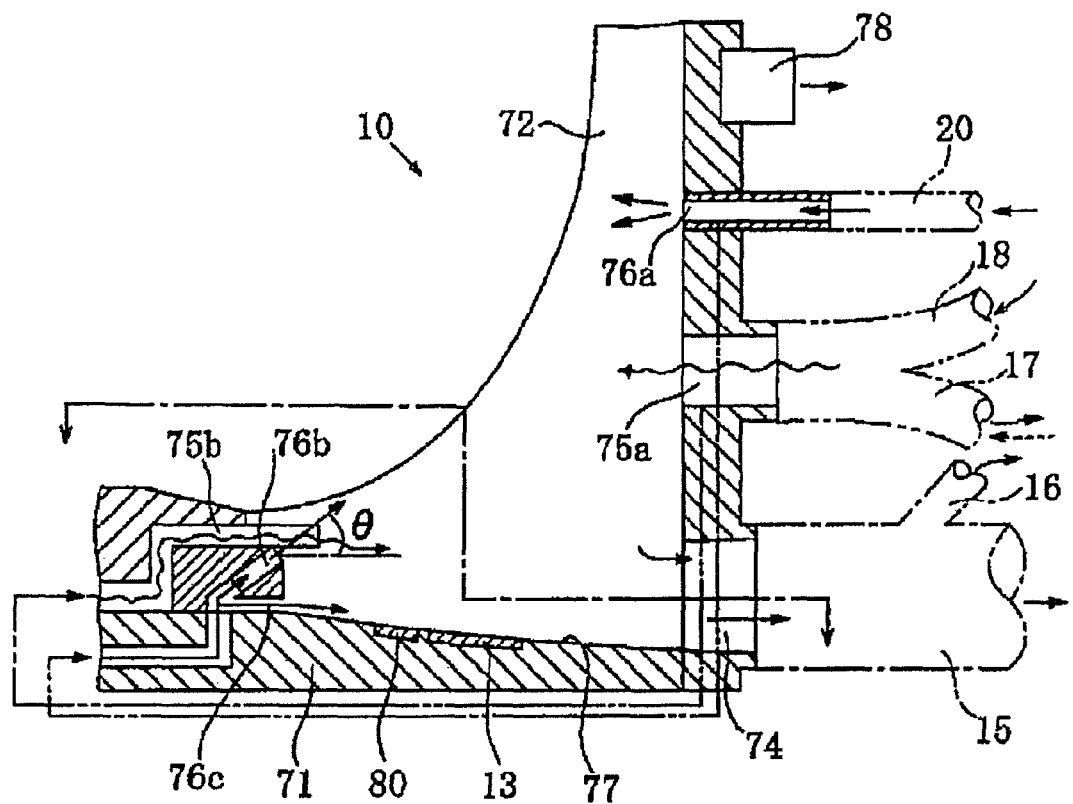
FIG. 5 shows a cross-section view lacking a part of the napkin cup main body 10 used for the processing equipment and methods relating to the present invention.
Figure 6:
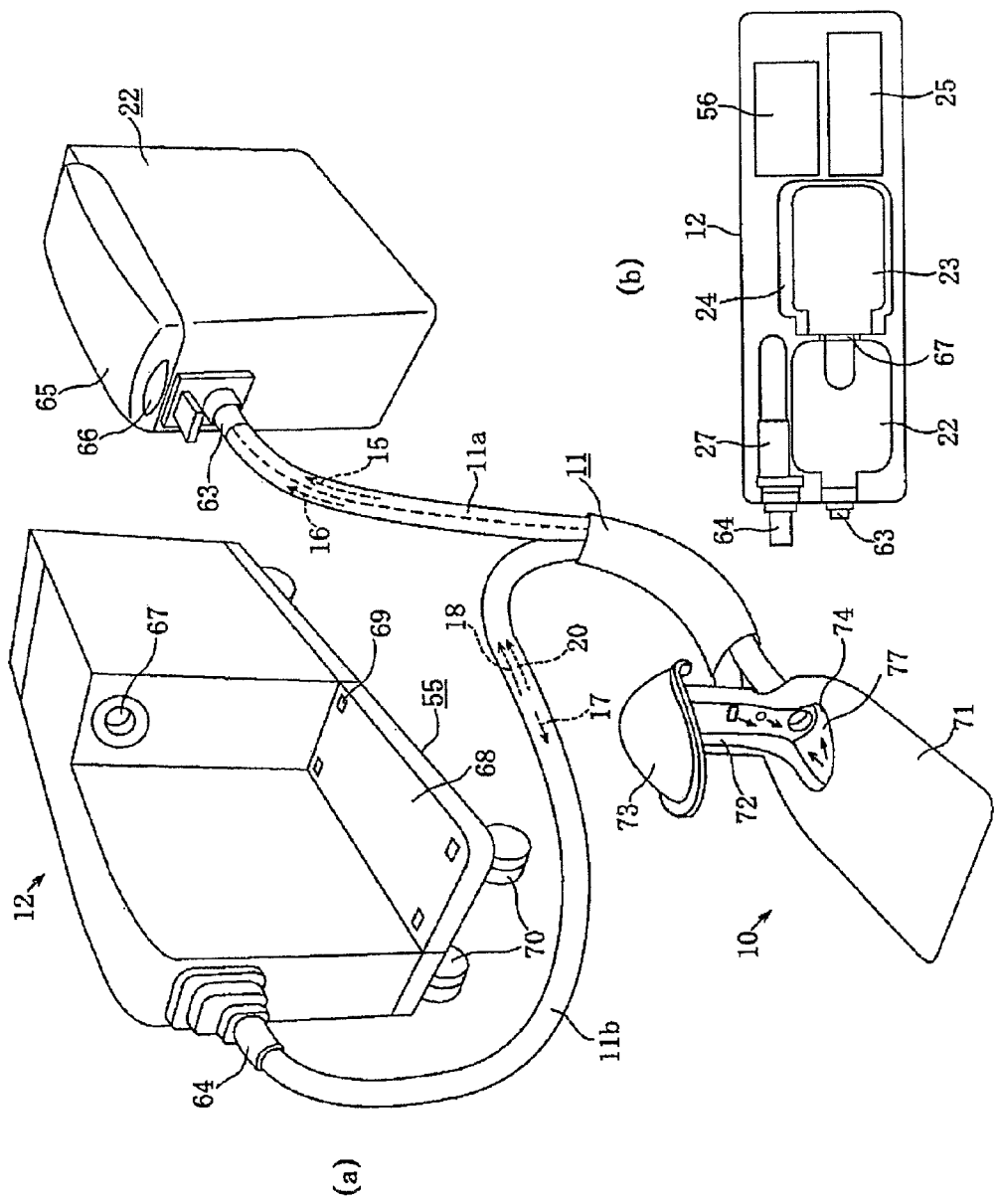
FIG. 6 shows the example 1 of the processing equipment of excretory substances and methods relating to the present invention, in which (a) shows a disassembled per view and (b) shows an illustration of arrangement examples of each unit.

The processing equipment of excretory substances of the present invention is shown as a schematic diagram in FIGS. 1 and 2 and as an oblique diagram in FIG. 6.

As known from these diagrams, the processing equipment of excretory substances of the invention comprises the napkin cup main body 10, device-house box 12, and hose unit 11 connecting these.

Said napkin cup main body 10 is shown in FIGS. 4, 5, 14 and 15 and is an approximately same as those described in said patent documents 1, 2, and 3. However, in the present invention, an odor sensor 80 as well as the defecation sensor 13, urination sensor 14 is equipped.

Said napkin cup main body 10 which is applied to a site between crotches of the person receiving care in side lying position via the napkin 54 comprises a bottom plate 71, an anterior plate 72, and a cover 73. A sewage discharge hole 74, a return air blowout hole 75a, discharge hole for rinse solution for the pubic site 76a, and a sensor connector 78 are equipped in ascending order from the lower edge of the anterior plate 72.

On said bottom plate 71, the concave part receiving excretory substances 77 is mounted adjacently to said sewage discharge hole 74, and the defecation sensor 13 is mounted at approximate center of the concave part receiving excretory substances 77. Multiple urination sensors are equipped at the outer circumference of the defecation sensor 13. Moreover, the odor sensor 80 is mounted at said concave part 77.

At the contrary side to the sewage discharge hole 74 of the concave part receiving excretory substances 77, a discharge hole of rinse solution for the anus 76b being adjacent to said discharge hole of rinse solution for the pubis site 76a and a discharge hole of rinse solution for the cup 76c are equipped. Moreover, at both the sides of the discharge hole of rinse solution for the anus 76b and the discharge hole of rinse solution for the cup 76c, a return air blowout hole 75b being adjacent to said return air blowout hole 75a is mounted.

Said defecation sensor 13 comprises a photo-reflector to detect stool's hardness and a distortion sensor or others, being installed at the bottom part of stool's falling, and controls to vacuum up excretory substances by the control panel unit 56 at the setting with higher suction power for higher signals of stool's hardness. Said urination sensor 14 has a pair of configuration with two contact points between which the resistance is measured to evaluate for presence or absence of urine and controls by the control panel unit 56 to calculate a necessary suction power according to degree of the signals.

Figure 7:
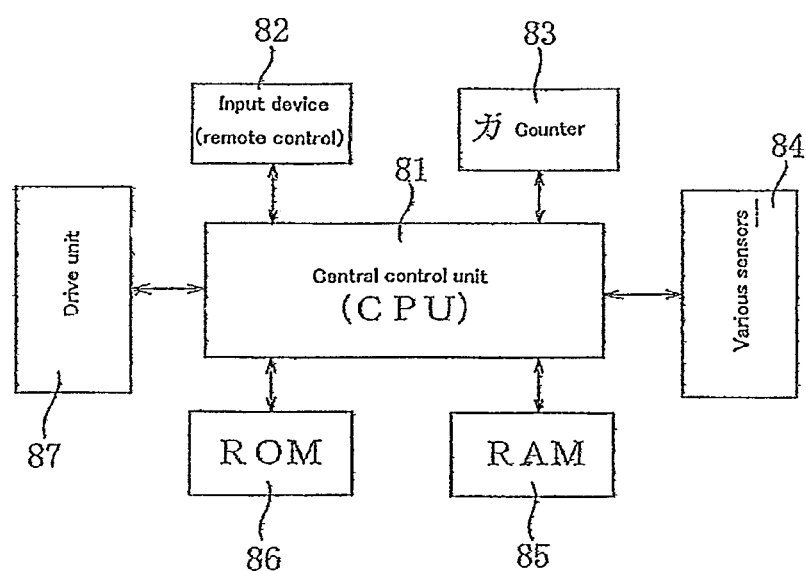
FIG. 7 shows a diagram of control circuit to control the processing equipment of excretory substances relating to the present invention.

Said control panel unit 56 comprises a central control unit 81, an input device 82, a counter 83, various sensors 84, a RAM 85, ROM 86, and a drive unit 87, as shown in FIG. 7, and controls various processing modes as shown in FIGS. 8-11.

Said input device 82 is used for switching to automatic or manual operation, directing various modes, setting or changing the temperature or the flow volume of rinse solution, and other direction, which can be configured by remote control.

Said various sensor 84 comprises the defecation sensor 13, the urination sensor 14, a temperature sensor 49, a bimetal 57, a water-level sensor 58, a negative pressure sensor 52, a temperature sensor 45, a water-level sensor 41, the odor sensor 80.

Said counter 83 calculates the number of urination and the number of times of cleaning etc. and memorizes at the RAM85.

Said RAM 85 memorizes data of the input device 82 or the counter 83 temporarily.

Said ROM 86 memorizes various control programs for processing as shown in FIGS. 8~11.

Said drive unit 87 comprises various driving units including the sewage-water tank unit 22, cleanup processing unit 23, suction motor unit 24, water supply unit 25, return air cooler 26, return box unit 27, and heater 44; and drives by output from said central control unit 81.

The cleaning hole equipped in the napkin cup main body 10 comprises the discharge hole of rinse solution for the anus mounted upward from said the bottom plate 71 and the discharge hole 76b of rinse solution for approximate flat pubic site 76a mounted from the anterior plate 72. Said discharge hole 76b is a discharge hole like plus shape (+) and said discharge hole 76a a discharge hole like minus shape (−). The direction of water discharge and position in the plus and minus shapes differs between males and females and among races, so that the napkin cup main body 10 can be exchanged according to the physical constitution.

The bottom plate 71 of the napkin cup main body 10 applied to the region covering from the coccygeal bone to the hip is made from a flexible material for the height and width directions of the person receiving care in order to prevent bed sore.

The napkin cup main body 10 is made from moderate or high resin such as polyamide series, urethane, polyethylene, polyester, alkid resin etc., is protected by the surface applied by fluorite resin or silicon resin to prevent from sewage, which reduces sewage to attach and to become tainted.

Said hose unit 11 comprises the sewage suction hose 15, the slight wind hose 16 diverging from the sewage suction hose 15, the return air hose 18 connected to the return air discharge hole 75a, the slight wind hose 17 diverging from the return air hose 18, and the rinse solution hose 20.

Said hose unit 11 comprises the sewage suction hose 15, the slight wind hose 16 diverging from the sewage suction 15, the return air hose 18 connected to the return air blowout hole 75a, the slight wind hose 17 diverging from the return air hose 18, and the rinse solution hose 20.

Said sewage suction hose 15 and slight wind hose 16 are connected to said sewage discharge hole 74 and held together as the hose 11a for sewage, and are combined with the sewage water tank unit 22 of the device-house box 12 by the hose connector 63 in a detachable manner.

The return air hose 18 and slight wind hose 17 connected to said return air blowout hole 75a and the rinse solution hose 20 connected to the discharge hole of rinse solution for the pubic site 76a are held together as the hose for water/air 11b and are combined with the water supply unit 25 of the device house box 12 and the return box unit 27 through the hose connector 64 in a detachable manner.

Said defecation sensor 13, said urination sensor 14, and 180 lead wires are connected to the control panel unit 56 from the hose connector 64 through the sensor connector 78.

To automatically clean the sewage carrier hose of the hose unit 11 by water, the nozzles such as those of the sewage suction hose 15 and slight wind hose 16 are designed to have shapes and directions with which water ejected can rotate in relevant hose to clean the inside of the hose.

Figure 16:
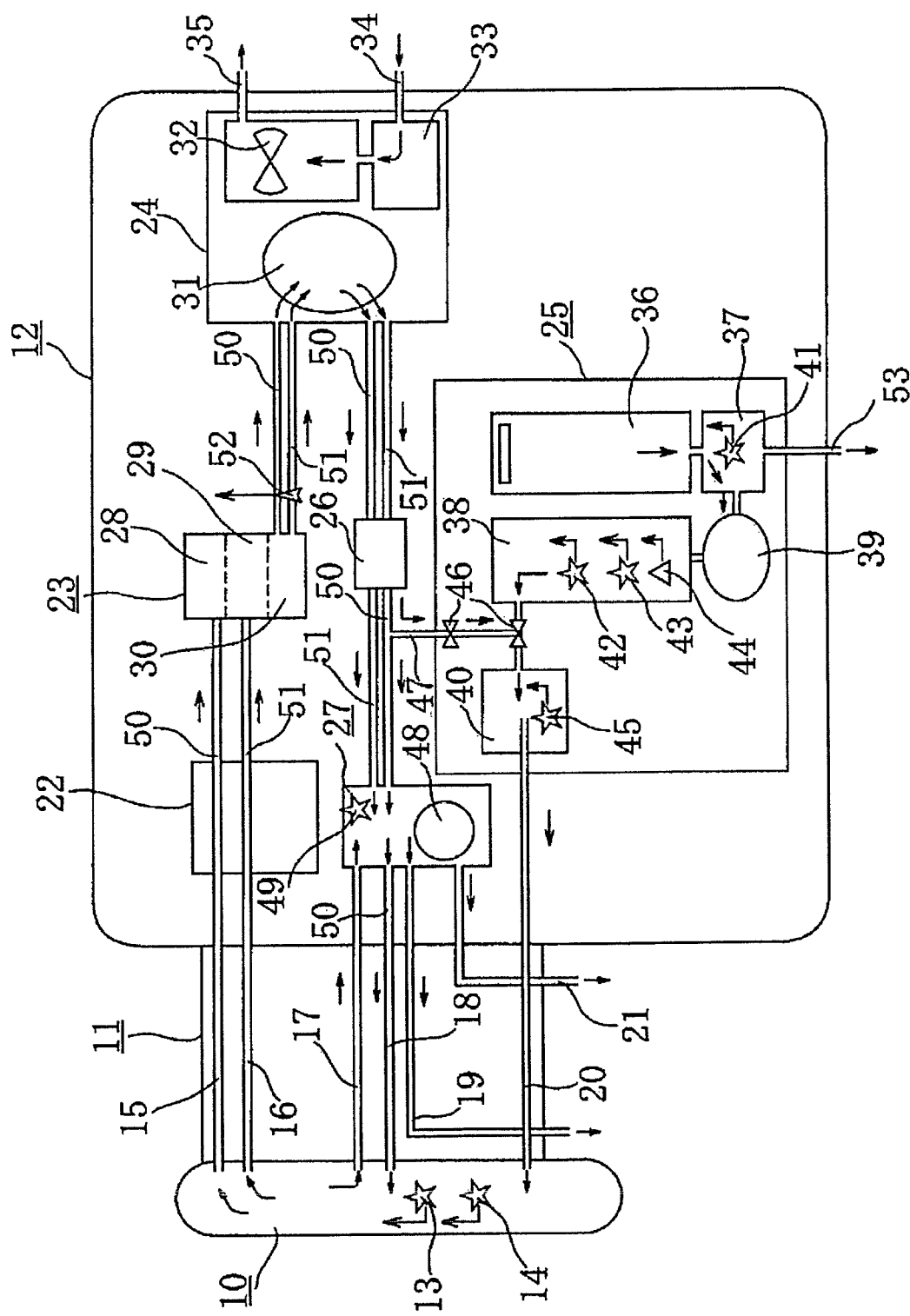
FIG. 16 shows a schematic diagram of conventional processing equipment of excretory substances.

Next, as shown in FIG. 16, similarly, the device hose box 12 comprises the sewage water tank 22, cleanup processing unit 23, suction motor unit 24, water supply unit 25, and return box unit 27. The cooling mechanism of cooling unit with circulating air 55 and the compactly assembled device house box 12 and easily detachable sewage water tank unit 22 are made improvements.

First of all, the configuration shown in FIG. 16 is explained, based on FIGS. 1 and 2.

Said sewage water tank unit 22 vacuums up and houses excretory substances and sewage water after cleaning by the suction motor 31 of the suction motor unit 24 described later. When air is vacuumed up from the inside of the sewage water tank 22 through the suction circulation tube 50 and the sewage suction hose 15 by the suction motor 31, excretory substances and sewage water after cleaning in the concave part receiving secretory substances 77 of the napkin cup main body 10 are vacuumed up and housed inside the sewage water tank 22. Inside the sewage water tank 22, the excretory substances and sewage water after cleaning are separated with gravity by work wind circulating in the suction circulation tube 50.

The cleanup processing unit 23 connected to the sewage water tank unit 22 equips a mist-eliminating filter 28, an odor-eliminating filter 29, and a disinfect filter 30. The negative pressure sensor 52 to detect for if gas tight of hoses connected to the napkin cup main body 10 is mounted at the suction circulation tube 50 inside the cleanup processing unit 23.

The suction circulation tube 50 and a slight-wind circulation tube 51 mounted along the suction circulation tube 50 pass through the housing of the suction motor unit 24 from the cleanup processing unit 23, connected to the suction motor 31 and led to the cooling box 61 of the cooling unit 55 through the discharge hole 59 from the suction motor unit 24.

The cooling fan 32 is installed at said suction motor 31. Air taken in from a cooling wind intake hole 34 cools down the suction motor 31 through the filter 33 and is discharged from a cooling wind discharge hole 35. The water-level sensor 58 is installed at the sewage water tank unit 22.

The suction motor 31, cooling fan 32, and filter 33 inside said suction motor unit 24 are covered by highly rigid and vibration proof materials and held with suspension on the vibration preventive board processed by vibration preventive materials such as vibration preventive rubber or by the vibration preventive spring 79. The water supply pump 39 is also installed in the same manner.

Said cooling box 61 which is flat and box-like is placed at the bottom of the main body of the device-house box 12 and this box body and inner partition plate 62 are made from metal plates with good heat conduction. The suction circulation tube 50 and slight wind circulation tube 51 which are led to the inside of the cooling box 61 bend as being divided by the partition plates 62 and then led outside from the discharge hole 60. As for said materials of metal plates with good heat conduction, aluminum extruded materials and aluminum rolled materials which can be processed easily are cheap and suitable for absorption and irradiation as well as coppers are suitable. Moreover, with of after alumite-processing, black color made by secondary-electrolyzation coloring increases the heat absorption and heat release more effectively.

The suction circulation tube 50 and slight wind circulation tube 51 led from said discharge hole 60 is led to the return box unit 27 inside the device house box 12. Among those, the main tube of the suction circulation tube 50 is connected to the napkin cup main body 10 through the return air hose 18 for about 90% of work wind returning. A part of the divergence tubes become the discharge hose 19, which discharges about 10% outside. The return box unit 27 equips the temperature sensor 49 and the bimetal 57.

Said water supply unit 25 equips the rinse solution tank 36, a supplementary tank 37, a hot water tank 38, a water supply pump 39, a valve 46 and a safety tank 40. Said hot water tank 38 equips the water-level sensor 42, temperature sensor 43, and heater 44. Said safety tank 40 equips the temperature sensor 45. The pipe at the discharge side of said valve 46 is connected to the napkin cup main body 10 through said rinse solution hose 20. A drainage tube 47 is mounted at said valve 46.

The control panel unit 56 is mounted in said device house box 12. At the input side of the control panel unit 56, various sensors are connected and drive control signals are transmitted to the output-side suction motor 31, cooling fan 32, water supply pump 39, valve 46, and slight wind motor 48.

Overall diagrammatic actions of the above configuration are explained. The detailed processing operation of each mode based on the flow charts shown in FIGS. 8~11 will be explained later.

First of all, the hot water tank 38 is filled up and if the sewage water tank 22 is empty is confirmed. In case that the hot water tank 38 is empty or the sewage water tank 22 is full, the sign as for the permission for processing operation becomes NO, and the alarm is displayed by signals from the water level sensor 42 or the water level sensor 58 to prevent the automatic operation condition.

The napkin cup main body 10 is applied to the region from the hip to the groin in the person receiving care via the napkin 54 and the start switch of the control panel unit 56 is turned on. In this condition, sensors or others (the water level sensor 41, water level sensor 42, temperature sensor 43, heater 44, temperature sensor 45, temperature sensor 49, negative pressure sensor 52, bimetal 57, water level sensor 58) become possible condition for processing operation under normal conditions. In non-operation condition of the suction motor 31, the slight wind motor 48 operates and the slight wind is vacuumed up to the slight wind motor 48 from the napkin cup main body 10 through the slight wind hose 16 and sight wind circulation tube 51, as shown by the dotted lines in FIGS. 1 and 2, being then sent from the slight motor 48 through the slight wind hose 17 to the napkin cup main body 10 from the return air blowout holes 75a and 75b. In addition, in the non-operation condition of the slight wind motor 48, the slight wind motor 48 can be operated continuously or intermittently for predetermined time for inhibition of the increase of inner temperature or electricity saving. The details will be explained later, based on FIG. 13.

Here, when excretory substances are detected by any of the defecation sensor 13, urination sensor 14 or odor sensor 80, after a certain time passes, hot water is sent from the rinse solution unit 25 to the napkin cup main body 10 through the rinse solution hose 20. The rinse solution unit 25 equips a hot water tank 38 having the heater 44 and temperature sensor 43.

Hot water from the discharge hole 76a of rinse solution for the pubic site in the napkin cup main body 10 is sprayed to clean the pubic site and hot water from the discharge hole of rinse solution for the anus 76b is sprayed to clean the anus. Hot water from the discharge hole of rinse solution for the cup 76c is sprayed to the concave part receiving excretory substances 77 to wash out the excretory substances. The sewage water and excretory substances are led to the discharge hole of sewage 74.

At the same time, when the suction motor 31 operates to vacuum up air from the suction circulation tube 50, the sewage water and excretory substances after cleaning are vacuumed up to the sewage water tank unit 22 through the discharge hole of sewage 74 and sewage suction hose 15. When air is vacuumed up from the inside of the sewage water tank 22, inside the sewage water tank 22, the excretory substances and sewage water vacuumed up are separated with gravity by work wind circulating through the suction circulation tube 50.

Here, the suction power of the suction motor 31 is set by the control panel unit 56 according to the values detected by the defecation sensor 13 and urination sensor 14. The output of the suction motor 31 ranges 400W-1kW, which is adjusted to become high, middle, or low level roughly.

The sewage water tank 22 equips the water level sensor 58 which is a limit sensor of sewage amount. When sewage reaches the limit line of the sewage tank 22, the signal is sent to the control panel unit 56 and displayed with alarm on the display board (not shown in the diagram). The alarm is notified to care personnel or nurses by telephone or wireless telephone. The sewage water tank 22 separates solid sewage, sewage water, and air.

The work wind 55 containing water which passed through the sewage water tank unit 22 passes through the cleanup processing unit 23 and is cleaned up. The filter box 23 comprises the mist eliminating filter 28, odor eliminating filter 29, and bacteria eliminating filter 30. About 0.3 μm or larger of particles are eliminated to prevent environmental contamination of surrounding by air's slight discharge and leakage from this equipment.

The work wind cleaned up is sent to the cooling box 61 in the cooling unit 55 through the suction motor 31.

Here, the suction motor 31 is cooled down in such a manner that outer air is vacuumed up from the intake hole of cooling wind 34 through the filter 33 by the sewage water tank unit 22 and the air is discharged from the discharge hole of cooling wind 35. However, the cooling down is designed because the suction motor 31 is isolated inside the sewage water tank unit 22 for preventing vibration and noises, so that heat caused by the operation cannot be released anywhere and over-heating of the suction motor 31 may cause operation failure or overheating of work wind flowing through the suction circulation tube 50 may cause burn injury of human body.

When the work wind returns to the napkin cup main body 10 applied to the person receiving care, it is desirable to be kept at about 30~42.

Thus, inside the cooling box 61, because the suction circulation tube 50 and slight wind circulation tube 51 bend in a space are divided off by the partition plate 62, the work wind is cooled down by heat exchange with outer air through the cooling box 61 and partition plate 62 and then discharged from the discharge hole 60.

As for work wind cooled down in the suction circulation tube 50, about 10% is released to outside through a partial discharge hose 19 in the return box unit 27, and 90% is sent to the napkin cup main body 10 through the return air hose 18. Slight wind from the slight wind circulation tube 51 and slight wind hose 17 is vacuumed up at the slight wind motor 48 and discharged from the slight wind discharge hose 21.

Partial air discharged undergoes bacteria elimination and disinfect through a high-performance filter (HEPA filter) or ultraviolet sterilizer.

Figure 8:
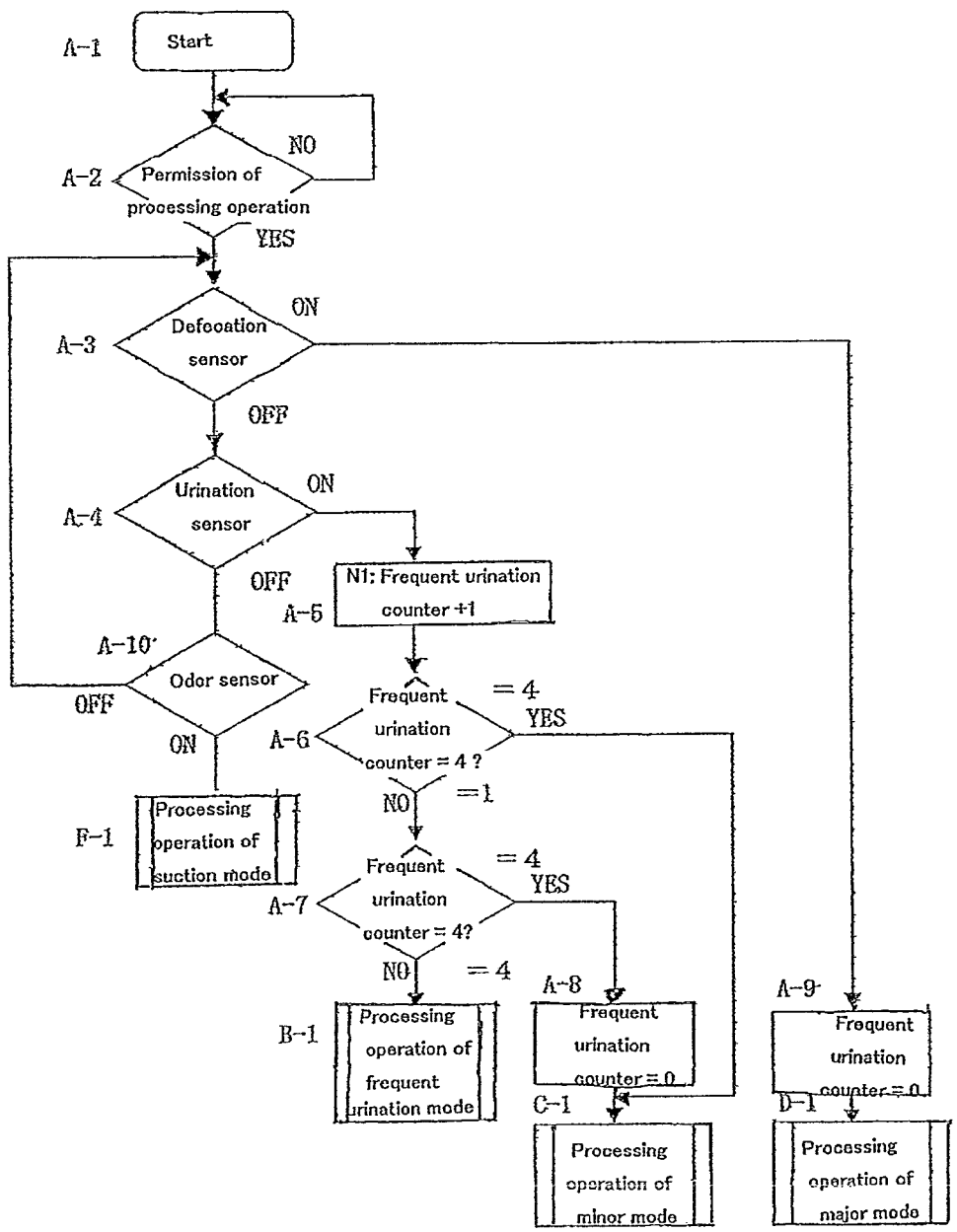
FIG. 8 shows a flow chart of the overall processing operation mode relating to the present invention.
Figure 9:
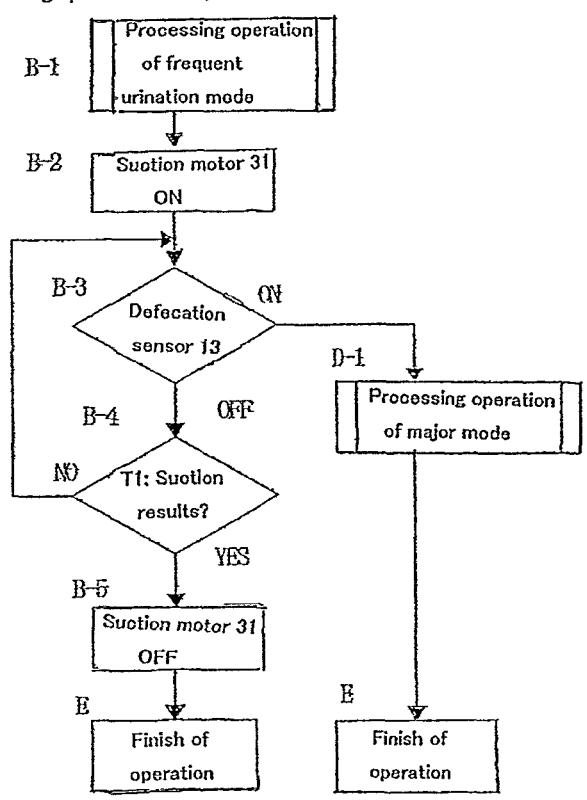
FIG. 9 shows a flow chart of the frequent urination processing operation mode shown in FIG.8.
Figure 10:
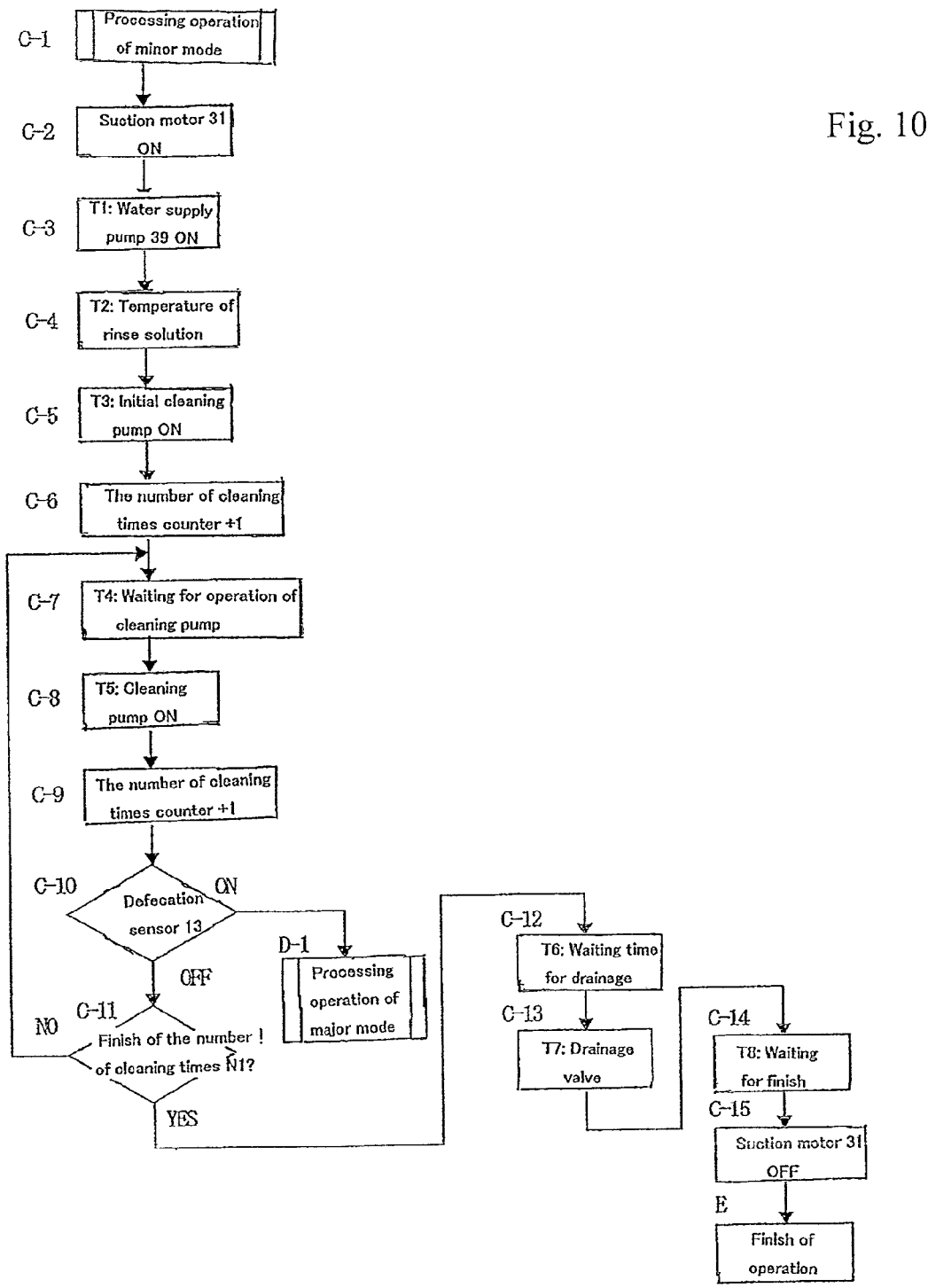
FIG. 10 shows a flow chart of the urination processing operation mode shown in FIG.8.

Next, various processing modes are explained, based on FIG. 8.

1. Transition of Automatic Processing Modes
A-1: Start signals are sent to the control panel unit 56 by input device 82.
A-2: Waiting until the temperatures of hot water, hot wind and temperatures of others inside the device house box 12 and the water level of the tank reach the set values, once the signal for permission of processing operation is transmitted, it becomes YES and then shifts to A-3.
A-3: If the defecation sensor 13 is at ON, a counter 83 is returned to A-9 to shift to D-1. If the sensor at OFF, it shifts to A-4.
A-4: If the urination sensor 14 is at ON, it shifts to A-5, and if the sensor is at OFF, it shifts to A-10.
A-5: The counter 83 calculates at every predetermined time (for example, one second).
A-6: If the counter 83 counts N1=4, it shifts to C-1, and with less than 4, it shifts to A-7.
A-7: If the counter 83 counts 4, the counter 83 is returned to 0 at A-10 to shift to C-1, and with less than 4, it shifts to B-1.
A-10: If the urination sensor 14 is at OFF in said A-4, it shifts to A-10. If the odor sensor 80 is at OFF in the A-10, it returns to A-3, and if the sensor is at ON, it shifts to F-1.
F-1: When the processing operation of the suction mode is started, the suction motor 31 drives, odor from the napkin cup main body 10 is vacuumed up, and the air from which odor is eliminated through the odor eliminating filter 29 in the cleanup processing unit 23 circulates.

2. Processing Operation of Frequent Urination Mode (FIG. 9)
B-1: The processing operation of frequent urination mode is started.
B-2: When the suction motor 31 is turned ON to start the suction, it shifts to
B-3: If the defecation sensor 13 is at ON, it shifts to D-1, and with OFF, it shifts to B-3.
B-4: The suction motor 31 continues to vacuum up for a predetermined time of T1, suction time (for example, 20 seconds), and when the time passes, it shifts to B-5.
B-5: The suction by the suction motor 31 is stopped to stop the processing operation of frequent urination mode.

The operation of frequent urination is carried out when any one of the following conditions is met.
(1) When the urination sensor 14 is detected within the predetermined time T11 (for example within 60 minutes) in previous minor operation mode.
(2) When the number of continuous operation of frequent operation mode is less than a set number N1 (for example, four times).

Remarks
(1) At manual operation, the operation of frequent urination is absent.
(2) During the time from stop to immediately after start, it usually becomes minor or major mode.
(3) When the number of the operation of frequent urination exceeds a set number N1 (for example, four times), it becomes the minor mode.

Release Conditions of Frequent Urination Mode
(1) When it becomes the stop mode
(2) When it operates with the major mode
(3) After the operation stopped, when continuous urination sensor Processing Operation of Minor Mode (FIG. 10)
C-1: The processing operation of minor mode is started.
C-2: Suction is started by the suction motor 31.
C-3: The water supply pump 39 is driven at a degree that the safety tank 40 of the hose water tank 38 is filled only during T1 time (for example, two seconds).
C-4: The temperature of rinse solution is evaluated for T2 time (for example, two seconds) by the temperature sensor 43.
C-5: Only for first time, the water supply pump 39 is driven for T3 time (for example, three seconds). Because water is absent in the length of the rinse solution hose 20 from the water supply pump 39 to the napkin cup main body 10, only the first time, the pump is driven for slightly longer time.
C-6: The number of cleaning is counted and +1 is added. On C-5 and C-6 processes, presence or absence of initial cleaning can be selected. When absence of initial cleaning is selected, it can be done not to be carried out it.
C-7: Only for T4 time (for example, 27 seconds), driving the water supply pump 39 is waited.
C-8: After passing T4 time (for example, 27 seconds), the water supply pump 39 is driven only for T5 time (for example, two seconds).
C-9: The number of cleaning is counted and +1 is added.
C-10: After the urination sensor 14 is turned ON, when the defecation sensor 13 is turned ON, it shifts to D-1 mode. If the defecation sensor 13 is at OFF, if the number of cleaning is N1=2 is evaluated. With less than 2, it returns to C-7 to wait, and with N1=2, it shifts to C-12.

C-11: Until the pressure of rinse solution decreases, water removal is waited only for T6 time (for example, two seconds), C-3: After the water removal time passed, the valve 46 is opened only for T7 time (for example, 25 seconds) to discharge the rinse solution from a region from the water removal tube 47 to the napkin cup main body 10.

C-14: Wind is sent only for T8 time (for example, 5 seconds) and the end is waited.

C-15: After T8, the suction motor 31 is turned off and the operation is then stopped.

Figure 11:
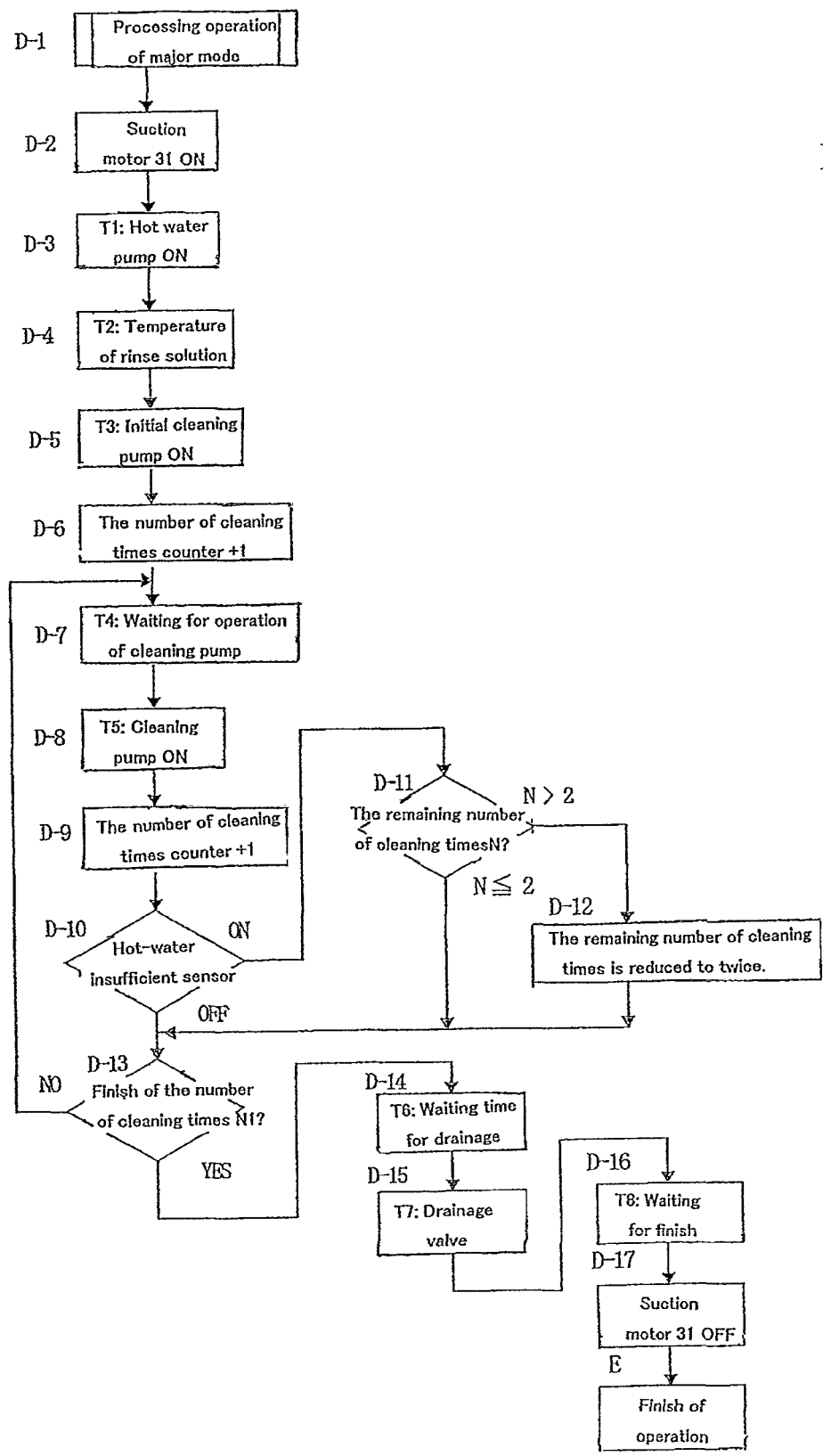
FIG. 11 shows a flow chart of the defection processing operation mode shown in FIG.8.

Major Mode Processing Operation (FIG. 11)

D-1: The major mode processing operation is started.

D-2: Suction is started by the suction motor 31.

D-3: The water supply pump 39 is driven at a degree to fill the safety tank 40 of the hot water tank 38 for only T1 time (for example, two seconds).

D-4: The temperature of rinse solution is evaluated by the temperature sensor 43 for T2 time (for example, two seconds).

D-5: The water supply pump 39 is driven first time for only T3 time (for example, four seconds).

D-6: The number of cleaning is counted and +1 is added.

D-7: Driving the water supply pump 39 is waited for only T4 time (for example, 26 seconds).

D-8: After T4 time (for example, 26 seconds) passes, the water supply pump 39 is driven for only T5 time (for example, four seconds).

D-9: The number of cleaning is counted and +1 is added.

D-10: Insufficiency of the water level in the hot water tank 38 is detected by the water level sensor 42. If it is insufficient (on), it shifts to D-11, and if it isn't insufficient (oft, it shifts to D-13.

D-11: If the number of remaining cleaning N is N>2, it shifts to D-12. With N 2, because the number of cleaning is a few, it shifts to D-13 to increase the number of cleaning.

D-12: With N>2 for the number of cleaning, because the cleaning has been already done three time or more and the water level in the hot water tank 38 is insufficient, the upper limit of the number of cleaning is reduced to twice, it shifts to D-13.

D-13: When the water level in the hot water tank 38 is not insufficient, if the number of cleaning is N1=4 is evaluated. If it less than 4, it returns to D-7 to repeat, and when it becomes N1=4, it shifts to D-14. When the water level in the hot water tank 38 is insufficient, it shifts to D-14 by direction from D-12 even if the number of cleaning is twice.

D-14: Drainage of water is waited for T6 time (for example, two seconds) until the pressure of rinse solution decreases.

D-15: After the time for drainage of water passes, the valve 46 is opened for only T7 time (for example, 25 seconds) to discharge the rinse solution of the length from the water removal tube 47 to the napkin cup main body 10.

D-16: Wind is sent for only T8 time (for example, five seconds) and the end is waited.

D-17: The suction motor 31 is turned off to finish the operation.

The processing equipment of excretory substances of the present invention comprises the device house box 12, cooling unit 55, sewage water tank unit 22, napkin cup main body 10, and hose unit 11, which are unified in a detachable manner. The device house box 12 comprises the cleanup processing unit 23, suction motor unit 24, water supply unit 25, return box unit 27, and control panel unit 56, which are unified in a detachable manner. The napkin cup main body 10 and sewage water tank unit 22 are connected by the hose connector 63 through the hose for sewage 11a in the hose unit 11 in a detachable manner. The napkin cup main body 10 and the return box unit 27 in the device house box 12 are connected by the hose connector 64 through the hose for water and air 11b in the hose unit 11 in a detachable manner. The sewage water tank unit 22 latches together with a locking part 69 on a set board 68 in the cooling unit 55 and is also mounted by a insert hole 67 in a detachable manner, so that the sewage water tank unit 22 is detached from the set board 68 and the hose for sewage 11a of the hose unit 11 is detached by the partition plate 62 to deliver the excretory substances for processing and a cover body 65 is opened by a knob 66 to take out the inner housing container of excretory substances (not shown in figure) and clean with washing out the excretory substances.

Thus, pipes and wires connecting the units are set in an integrated manner and in a one-touch detachable manner, which facilitates to exchange the units such as due to failure or repair.

When the water in the hot water tank 38 is used, water is sent from the rinse solution tank 36 to the hot water tank through the supplementary tank 37 by pressure from the water supply pump 39 to be filled up. The supplementary tank 37 equips the water level sensor 41 and when it becomes empty, the alarm is displayed on the control panel unit 56.

The control panel unit 56 enables to wash the hip of the person receiving care by hands and use for washing the pipes of this equipment by rinse solution from the rinse solution hose 20.

When the suction motor 31 doesn't operate under an ordinary operation condition in which excretory substances are not detected, the slight wind motor 48 is operating and the return air is sent to the hip and groin part of the person receiving care through the return air hose 18 to dry the region and also dry the pipes of the equipment. That is, the slight wind motor 48 operates and the slight wind circulates through the slight wind hose 16, slight wind circulation tube 51, cooling box 61, and slight wind hose 17 in hose unit 11. Even if the inner temperature of the suction motor 31 cannot be released anywhere to cause overheating of the suction motor 31 when the suction motor 31 stops instantly after its high-speed operation, the above configuration enables to prevent it.

Air of the slight wind motor 48 inside the return box unit 27 is set in such a manner that the air becomes an appropriate temperature to human body by the bimetal 57 and if the temperature exceeds the appropriate temperature, the slight wind motor 48 rotates inversely to vacuum up the air in the napkin cup main body 10 from the slight wind hose 17 and discharges it outside by the slight wind discharge hose 21.

At the time of the operation of the suction motor 31 (at the sewage processing), about 10% of air as constantly circulating work wind is discharged and the shortage is taken up from the gap between the napkin 54 attached to the napkin cup main body 10 and the hip of the person receiving care.

In said cooling unit 55, a fan as well as the partition plate 62 can be mounted to increase the cooling effect.

When there is no signal from the defecation sensor 13 and urination sensor 14 to the control panel unit 56 and it is considered that the urination and defecation for set time (for example, six hours) or longer during times other than sleeping time are not conducted, the alarm can be displayed on the control panel unit 56 to notify it to care personnel or nurses.

Figure 13:
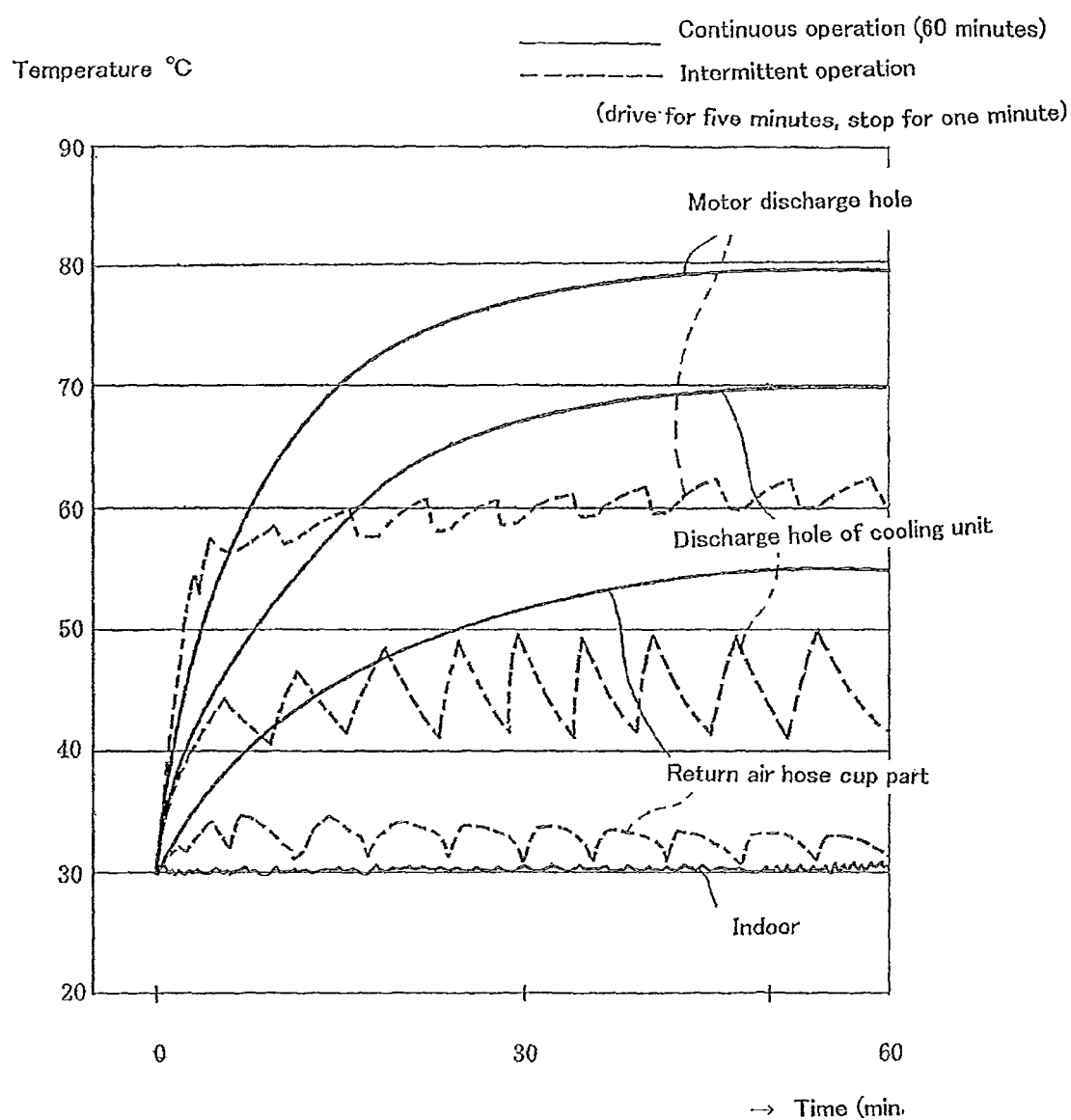
FIG. 13 shows a temperature property figure at the time of continuous operation and the time of intermittent operation by the processing equipment of excretory substances and methods relating to the present invention.
Figure 14:
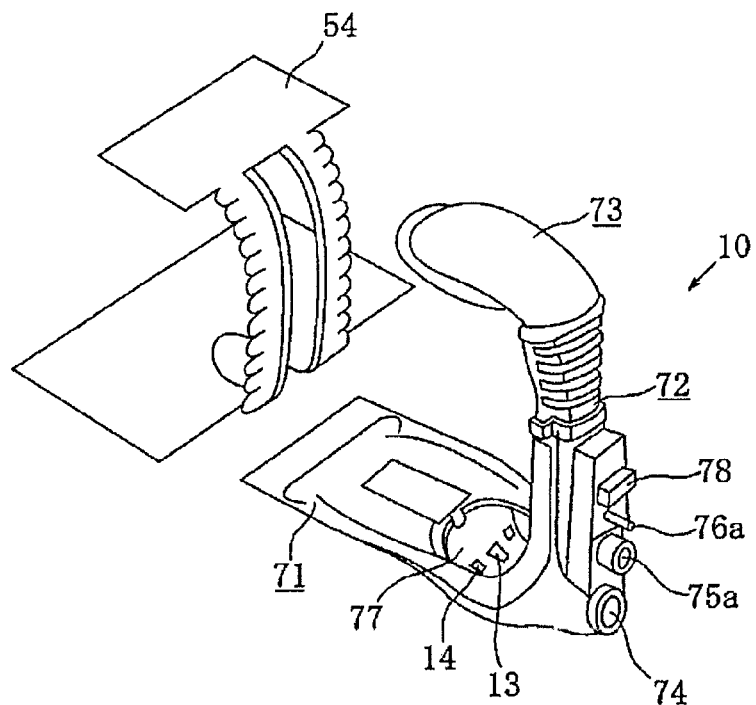
FIG. 14 shows oblique perspective figures of the napkin cup main body 10 and napkin 54.
Figure 15:
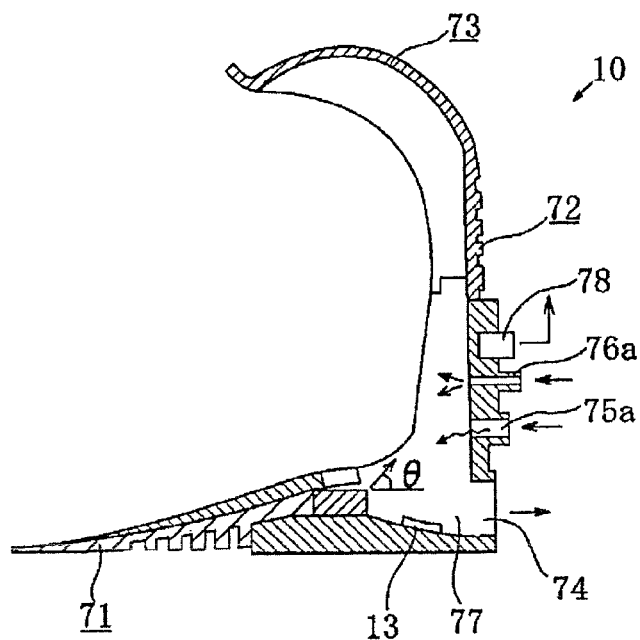
FIG. 15 shows a cross-section of the napkin cup main body 10.

FIG. 13 shows characteristic curves of the motor discharge hole, the discharge hole of the cooling unit, and return air hose cup part in the processing equipment of excretory substances of the present invention. The solid line indicates the characteristic curve of continuous suction operation for one hour, and the dotted line indicates of intermittent operation with five-minute operation and one-minute stop.

The temperature of the motor discharge hole 59 increase up to 80 in the continuous operation and 58~62 in the intermittent operation.

The temperature of the discharge hole of the cooling unit 60 increases up to 70 in the continuous operation and about 50 in the intermittent operation.

The temperature felt by human body in the return air hose cup part increases up to 55 in the continuous operation and 31~35 in the intermittent operation.

As for the motor discharge hole 59, when the suction motor 31 stops, the temperature without the cooling unit 55 in the continuous operation increases to about 100. On the other hand, the equipment of the present invention equips the cooling unit 55, so that the temperature can be suppressed to about 70. Actually, the one-hour continuous operation is absent.

Figure 12:
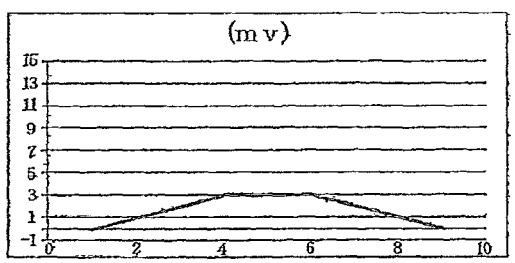
FIG. 12 (a)-(e) show output wave shapes of each sensor by the processing equipment of excretory substances and methods relating to the present invention.
Figure 12:
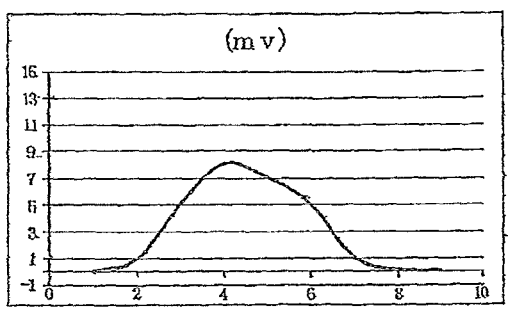
Figure 12:
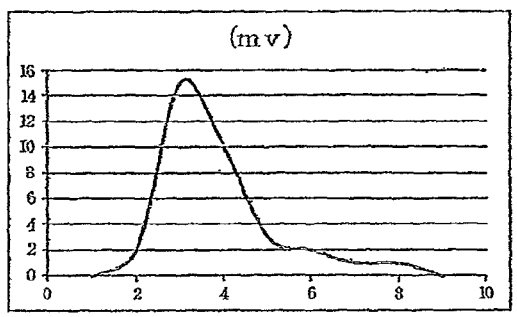
Figure 12:
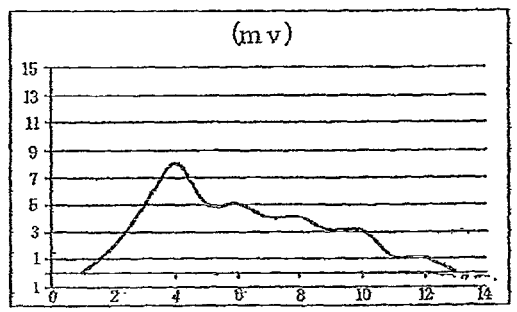
Figure 12:
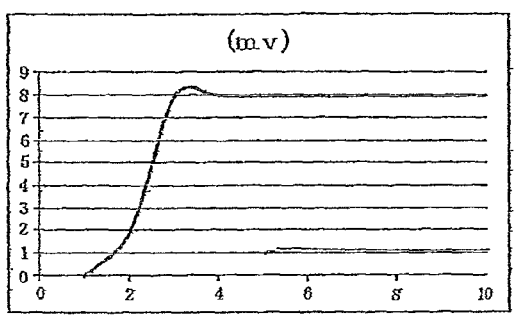

FIG. 12 (*a*) shows voltage wave shapes when the urination sensor 14 detects the urine. The voltage wave shapes are small for a long time. Moreover, in case of urine, the urine is re-confirmed by conduction of the urination sensor 14. In such signals, the control panel unit 56 controls to supply water until an appropriate amount is obtained and vacuum up at a level small.

FIG. 12 (*b*) shows wave shapes when the defecation sensor 13 detects soft stool. In case that the voltage level is so relatively low that the urination sensor 14 doesn't detect it, the control panel unit 56 controls to supply water until an appropriate amount is obtained and vacuum up at the level middle. However, generally, it is likely that stool and urine are ejected at a same time, so that the evaluation is conducted by the balance between the resistance value of the urination sensor 14 and the voltage of the defecation sensor 13. In case of such signals, the control panel unit 56 controls to supply water until an appropriate amount is obtained and vacuum up at the level middle.

FIG. 12 (*c*) shows voltage wave shapes when the defecation sensor 13 detects hard stool. If the voltage is high for a short time and the resistance value of the urination sensor 14 is high, it is considered that urine is absent. In such signal case, the control panel unit 56 controls to supply water until an appropriate amount is obtained and vacuum up at the level high.

FIG. 12 (*d*) shows normal voltage wave shapes when usual sewage water detected by the negative pressure sensor 52 inside the cleanup processing unit 23. The suction action is evaluated to be normal and the hip of the person receiving care is dried with slight wind.

FIG. 7 (*e*) shows voltage wave shapes when hard or large amount of stool detected by the negative pressure sensor 52 inside the cleanup processing unit 23 is vacuumed up by ordinary suction power. Those are voltage wave shapes when the suction cannot be done smoothly. In such signal case, the control panel unit 56 displays the alarm or notify it to care personnel and discharges sewage water by manual work.

In case of severe persons receiving care such as with unconsciousness, when the equipment collecting biological information and transmitting them which the inventers of the present invention proposed previously as patent No. 2009-188505 (published unexamined patent application NO. 2010-284498) is combined with the processing equipment of excretory substances of the present invention, being placed at a site between beds, information of urination and defecation information and biological abnormalities in the person receiving care can be obtained, so that degree of urination/defecation's desire, progressive or recovery degree of pathologic condition or sudden changes in pathologic condition in the person receiving care can be understood without installing a big-scale biological information system.

EXPLANATIONS OF LETTERS OR NUMERALS

10 . . . Napkin cup main body, 11 . . . Hose unit, 12 . . . Device house box, 13 . . . Defecation sensor, 14 . . . Urination sensor, 15 . . . Sewage suction hose, 16 . . . Slight wind hose, 17 . . . Slight wind hose, 18 . . . Return air hose, 19 . . . Partial discharge hose, 20 . . . Rinse solution hose, 21 . . . Slight wind discharge hose, 22 . . . Sewage water tank unit, 23 . . . Cleanup processing unit, 24 . . . Suction motor unit, 25 . . . Water supply unit, 26 . . . Return air cooler, 27 . . . Return box unit, 28 . . . Mist-eliminating filter, 29 . . . Odor-eliminating filter, 30 . . . Disinfect filter, 31 . . . Suction motor, 32 . . . Cooling fan, 33 . . . Filter, 34 . . . Cooling wind intake hole, 35 . . . Cooling wind discharge hole, 36 . . . Rinse solution tank, 37 . . . Supplementary tank, 38 . . . Hot water tank, 39 . . . Water supply pump, 40 . . . Safety tank, 41 . . . Water level sensor, 42 . . . Water level sensor, 43 . . . Temperature sensor, 44 . . . Heater, 45 . . . Temperature sensor, 46 . . . Valve, 47 . . . Drainage tube, 48 . . . Slight wind motor, 49 . . . Temperature sensor, 50 . . . Suction circulation tube, 51 . . . Slight wind circulation tube, 52 . . . Negative pressure sensor, 53 . . . Drain, 54 . . . Napkin, 55 . . . Cooling unit, 56 . . . Control panel unit, 57 . . . Bimetal, 58 . . . Water level sensor, 59 . . . Discharge hole, 60 . . . Discharge hole, 61 . . . Cooling box, 62 . . . Partition plate, 63 . . . Hose connector, 64 . . . Hose connector, 65 . . . Cover body, 66 . . . Knob, 67 . . . Insert hole, 68 . . . Set board, 69 . . . Locking part, 70 . . . Caster, 71 . . . Bottom plate, 72 . . . Anterior plate, 73 . . . Cover part, 74 . . . Sewage discharge hole, 75*a*, 75*b* . . . Return air blowout hole, 76*a* . . . Discharge hole of rinse solution for the pubic site, 76*b* . . . Discharge hole of rinse solution for the anus, 76*c* . . . Discharge hole of rinse solution for the cup, 77 . . . Concave part receiving excretory substances, 78 . . . Sensor connector, 79 . . . Vibration preventive spring, 80 . . . Odor sensor, 81 . . . Central control unit (CPU), 82 . . . Input device remote control 83 . . . Counter, 84 . . . Various sensors, 85 . . . RAM, 86 . . . ROM 87 . . . Drive unit

The invention claimed is:

1. A processing equipment of excretory substances of a urinary organ, comprising a sewage water tank unit, a cleanup processing unit, a suction motor unit, a water supply unit, and a return box unit in a device house box connected to a napkin cup main body by a hose unit;

in which rinse solution sent from a water supply pump in said water supply unit is sprayed to the inside of the napkin cup main body, in which the urinary organ and excretory substances of the urinary organ are washed in the napkin cup main body, in which a suction motor, closed and isolated inside said suction motor unit, generates a suction wind that vacuums up sewage, in which the sewage is divided into excretory substances and rinse solution that is housed separately in said sewage water tank unit, and in which said suction wind is filtered in the cleanup processing unit and returned to said napkin cup main body through the suction motor and return box unit by suction circulation tube;

wherein said suction circulation tube is led to a cooling unit mounted outside said device house box from the discharge side of said suction motor, is cooled down by heat exchange with outer air inside the cooling unit, and then returned to said return box unit;

wherein said cleanup processing unit, the suction motor unit, the water supply unit, and the return box unit are made independent units and housed inside the device house box and also connected in order in a detachable manner; and wherein said sewage water tank unit is separated from said device house box, made a unit, and connected to said cleanup processing unit in a detachable manner.

2. The processing equipment of excretory substances according to claim 1, wherein the cooling unit comprises a heat-conductive, metal, cooling box., in which the suction circulation tube is arranged.

3. The processing equipment of excretory substances according to claim 2, in which a first wind circulation tube is mounted along the suction circulation tube and forms a loop path from the napkin cup main body to the napkin cup main body through the sewage water tank unit, cleanup processing unit, cooling unit, and return box unit; and a first wind motor by which a first wind for drying circulates when the suction motor doesn't operate is mounted at the first wind circulation tube inside said return box unit.

4. The processing equipment of excretory substances according to claim 3, having multiple fins conducting heat exchange with outer air for the suction circulation tube and first wind circulation tube inside the cooling box.

5. The processing equipment of excretory substances according to claim 3, having a bimetal equipped inside the return box unit, by which when air circulating by the first wind motor exceeds a first temperature set in advance, the first wind motor rotates inversely to vacuum up the air heated in the napkin cup main body from a first wind hose and then discharge outside at a first wind discharge hose.

6. The processing equipment of excretory substances according to claim 1, in which a partial discharge hose is connected to the suction circulation tube to discharge a part of suction wind circulating and the same volume of air as discharged air is vacuumed up from outside at the napkin cup main body.

7. The processing equipment of excretory substances according to claim 1, having a flat cooling box, doubled with a seat on which the device house box and the sewage water tank unit are placed, and having a caster mounted at a bottom face.

8. The processing equipment of excretory substances according to claim 1, having a negative pressure sensor equipped in the cleanup processing unit to detect if airtightness of the hoses connected to the napkin cup main body is maintained.

9. The processing equipment of excretory substances according to claim 1 having the water supply unit comprising a rinse solution tank, a supplementary tank, a water supply pump, a hot water tank, a valve, and a safety tank; in which a water level sensor is installed at said supplementary tank, a water level sensor, a temperature sensor, and a heater to produce hot water are installed at said hot water tank, and a temperature sensor is installed at said safety tank.

10. The processing equipment of excretory substances according to claim 1, in which the suction motor operates intermittently with a unit of several minutes each for driving and stop.

11. A processing equipment of excretory substances of a urinary organ, comprising:

a sewage water tank unit, a cleanup processing unit, a suction motor unit, a water supply unit, and a return box unit housed in a device house box, wherein a napkin cup main body and the device house box are connected by a hose unit, wherein rinse solution sent from a water supply pump in said water supply unit is sprayed to an inside of the napkin cup main body when at least one of a urination sensor and a defecation sensor inside said napkin cup main body detects the urinary organ or excretory substances inside the napkin cup main body, wherein the sewage is vacuumed up by a suction wind of a suction motor in said suction motor unit and divided into secretory substances and cleaning water which are housed separately, only said suction wind is filtered in the cleanup processing unit and returned to said napkin cup main body through the suction motor and return box unit by a suction circulation tube; and wherein said processing equipment is configured to operate in a plurality of modes including a frequent urination mode during which the suction motor drives when the sensed signals are shorter than a set time of said urination sensor without sensed signals of said defecation sensor; a minor mode that the suction motor drives when sensed signals are higher than a set time of said urination sensor; and a major mode that the suction motor drives when sensed signals of said defecation sensor are present.

12. The processing equipment of excretory substances according to claim 11, in which in the frequent urination mode, the suction motor drives when sensed short signals at each set time of the urination sensor are less than set number of times.

13. The processing equipment of excretory substances according to claim 11, in which in the minor mode, when sensed short signals at each set time of urination sensor are higher than set number of times, the suction motor drives intermittently to clean multiple times.

14. The processing equipment of excretory substances according to claim 11, in which in the major mode, when sensed signals of the defecation sensor are present and the suction motor drives intermittently to clean multiple time, when the rinse solution is insufficient, set number of times is reduced to clean.

15. A processing equipment of excretory substances of a urinary organ, comprising:

a sewage water tank unit, a cleanup processing unit, a suction motor unit, a water supply unit, and a return box unit housed in a device house box, wherein a napkin cup main body and the device house box are connected by a hose unit, wherein rinse solution sent from a water supply pump in said water supply unit is sprayed to an inside of the napkin cup main body when at least one of a urination sensor and a defecation sensor inside said napkin cup main body detects the urinary organ or excretory substances inside the napkin cup main body, wherein the sewage is vacuumed up by a suction wind of a suction motor in said suction motor unit and divided into secretory substances and cleaning water which are housed separately, only said suction wind is filtered in the cleanup processing unit and returned to said napkin cup main body through the suction motor and return box unit by a suction circulation tube;

wherein a concave part receiving excretory substances is mounted in the napkin cup main body;

wherein a defecation sensor and an urination sensor are equipped at the concave part, said defecation sensor is mounted at a site of stool's falling, and comprises a first sensor to detect stool's hardness in order to control the suction of excretory substances at a setting of suction power with a higher suction power for higher signals of stool's hardness by a control panel unit; and wherein said urination sensor comprises a second sensor that evaluates for presence or absence of urine and has two contact points to control at the control panel unit in order to calculate a necessary suction power for vacuuming up excretory substances according to the degree of the signals and measures the resistance between the two points.

16. The processing equipment of excretory substances according to claim 15, having the napkin cup main body made from resin, in which at least the surface of the concave part receiving excretory substances is protected by a coating material from the sewage.

17. The processing equipment of excretory substances according to claim 15, in which a water level sensor for notifying a full condition of excretory substance is installed inside the sewage water tank unit.

18. The processing equipment of excretory substances according to claim 15, in combination with a first unit, the first unit for collecting and transmitting biological data about the person receiving care and being located by the napkin cup main body.

19. A processing equipment of excretory substances of a urinary organ, comprising:

a sewage water tank unit, a cleanup processing unit, a suction motor unit, a water supply unit, and a return box unit housed in a device house box;

wherein a napkin cup main body and the device house box are connected by a hose unit;

wherein rinse solution sent from a water supply pump in said water supply unit is sprayed to an inside of the napkin cup main body when at least one of a urination sensor and a defecation sensor inside said napkin cup main body detects the urinary organ or excretory substances inside the napkin cup main body;

wherein the sewage is vacuumed up by a suction wind of a suction motor in said suction motor unit and divided into secretory substances and cleaning water which are housed separately, only said suction wind is filtered in the cleanup processing unit and returned to said napkin cup main body through the suction motor and return box unit by a suction circulation tube; and wherein the suction motor, a cooling fan, and a filter inside the suction motor unit are covered by a first vibration-suppression material, placed on a vibration-preventive board having a second vibration preventive material, and held with suspension by a vibration-preventive spring.

20. The processing equipment of excretory substances according to claim 19, wherein the cooling unit comprises a heat-conductive, metal, cooling box, in which the suction circulation tube is arranged.

* * * * *